US012635980B2

(12) United States Patent
Hunter et al.

(10) Patent No.: US 12,635,980 B2
(45) Date of Patent: May 26, 2026

(54) METHOD OF EMPLOYING A MEDICAL APPARATUS WITH TRANSLATABLE IMAGING DEVICE FOR REAL-TIME CONFIRMATION OF INTERCEPTION OF TARGET TISSUE

(71) Applicant: Veran Medical Technologies, Inc., St. Louis, MO (US)

(72) Inventors: Mark Hunter, St. Louis, MO (US); Troy Holsing, Boulder, CO (US)

(73) Assignee: Veran Medical Technologies, Inc., St. Louis, MO (US)

( * ) Notice: Subject to any disclaimer, the term of this patent is extended or adjusted under 35 U.S.C. 154(b) by 80 days.

(21) Appl. No.: 18/522,605

(22) Filed: Nov. 29, 2023

(65) Prior Publication Data

US 2024/0206849 A1 Jun. 27, 2024

Related U.S. Application Data

(63) Continuation of application No. 17/504,165, filed on Oct. 18, 2021, now Pat. No. 11,864,946, which is a
(Continued)

(51) Int. Cl.
*A61B 8/00* (2006.01)
*A61B 5/00* (2006.01)
(Continued)

(52) U.S. Cl.
CPC .............. *A61B 8/445* (2013.01); *A61B 5/064* (2013.01); *A61B 5/066* (2013.01); *A61B 5/6852* (2013.01); *A61B 8/0841* (2013.01); *A61B 8/085* (2013.01); *A61B 8/12* (2013.01); *A61B 10/04* (2013.01); *A61B 18/1492* (2013.01); *A61B 5/0066* (2013.01); *A61B*

*5/0084* (2013.01); *A61B 2017/0034* (2013.01); *A61B 2017/00809* (2013.01); *A61B 17/3478* (2013.01); *A61B 2018/00577* (2013.01);
(Continued)

(58) Field of Classification Search
None
See application file for complete search history.

(56) References Cited

U.S. PATENT DOCUMENTS

| | | | | |
|---|---|---|---|---|
| 8,690,776 B2 * | 4/2014 | Razzaque | .............. | A61B 34/20 |
| | | | | 600/407 |
| 2013/0225997 A1 * | 8/2013 | Dillard | ............... | A61B 10/0283 |
| | | | | 29/896.9 |
| 2014/0142418 A1 * | 5/2014 | Gurley | .................. | A61M 25/09 |
| | | | | 600/424 |

* cited by examiner

*Primary Examiner* — Yi-Shan Yang
(74) *Attorney, Agent, or Firm* — Dykema Gossett PLLC

(57) ABSTRACT

A method of generating an image of a medical instrument using a medical apparatus includes a catheter, a medical instrument assembly, and an imaging assembly. The catheter has a first working channel terminating with a first distal exit, and a second working channel terminating with a second distal exit. The medical instrument assembly has a medical instrument adapted to be housed within the first working channel and adapted to be extendable through the first distal exit to an extended position beyond the first distal exit to intercept a target tissue. The imaging assembly includes an imaging device adapted to be housed within the second working channel and is extendable through the second distal exit to an extended position beyond the second distal exit. The imaging device is adapted to generate an image in an image plane of the distal end of the medical instrument when the distal end of the medical instrument is extended out the first distal exit.

18 Claims, 23 Drawing Sheets

Related U.S. Application Data continuation of application No. 16/545,401, filed on Aug. 20, 2019, now Pat. No. 11,160,532, which is a continuation of application No. 14/708,489, filed on May 11, 2015, now abandoned.

(51) Int. Cl.

| | |
|---|---|
| *A61B 5/06* | (2006.01) |
| *A61B 8/08* | (2006.01) |
| *A61B 8/12* | (2006.01) |
| *A61B 10/04* | (2006.01) |
| *A61B 18/14* | (2006.01) |
| *A61B 17/00* | (2006.01) |
| *A61B 17/34* | (2006.01) |
| *A61B 18/00* | (2006.01) |
| *A61B 18/02* | (2006.01) |
| *A61B 18/04* | (2006.01) |
| *A61B 18/18* | (2006.01) |
| *A61B 18/24* | (2006.01) |
| *A61B 34/20* | (2016.01) |

(52) U.S. Cl.

CPC . *A61B 2018/0212* (2013.01); *A61B 2018/048* (2013.01); *A61B 2018/1861* (2013.01); *A61B 18/24* (2013.01); *A61B 2034/2051* (2016.02)

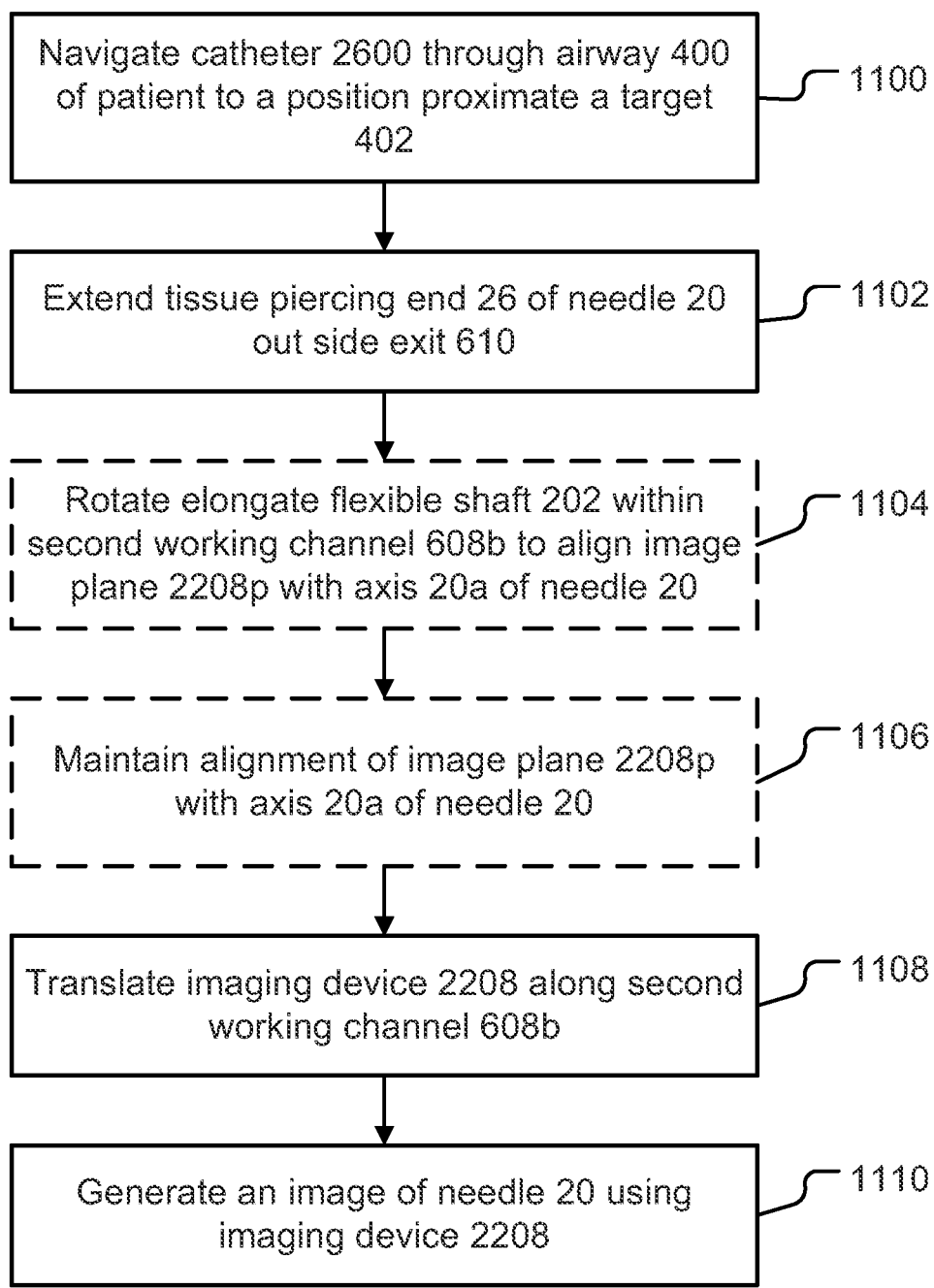

Navigate catheter 2600 through airway 400 of patient to a position proximate a target 402 — 1100

Extend tissue piercing end 26 of needle 20 out side exit 610 — 1102

Rotate elongate flexible shaft 202 within second working channel 608b to align image plane 2208p with axis 20a of needle 20 — 1104

Maintain alignment of image plane 2208p with axis 20a of needle 20 — 1106

Translate imaging device 2208 along second working channel 608b — 1108

Generate an image of needle 20 using imaging device 2208 — 1110

FIG. 9

Navigate catheter 3600 through airway 400 of patient to a position proximate a target 402 — 1200

Extend tissue piercing distal end 26 of needle 20 out side exit 610 — 1202

Generate an image of needle 20 using imaging device 3208 — 1204

28,228

606

602a

60c

19

20, 220

18a

18b

26

610

608a

606

602a

60c

19

18a

18b 28,228

610

20, 220

26    608a

606

602a

19

18a 28,228

610

20, 220

60c 26
18b

METHOD OF EMPLOYING A MEDICAL APPARATUS WITH TRANSLATABLE IMAGING DEVICE FOR REAL-TIME CONFIRMATION OF INTERCEPTION OF TARGET TISSUE

FIELD OF THE INVENTION

This invention relates generally to the utilization of medical instruments and systems and, more particularly, to apparatuses and systems associated with a range of medical procedures for detecting, sampling, staging and/or treating target tissues in the lungs of a patient.

BACKGROUND OF THE INVENTION

Image guided surgery (IGS), also known as image guided intervention (IGI), enhances a physician's ability to locate instruments proximate to and/or within anatomy during a medical procedure. IGS can include 2-dimensional (2D), 3-dimensional (3D), and 4-dimensional (4D) applications. The fourth dimension of IGS can include multiple parameters either individually or together such as time, motion, electrical signals, pressure, airflow, blood flow, respiration, heartbeat, and other patient measured parameters.

Navigation systems are used with image guided surgery to track the positions of the medical instruments in the body of a patient. The positions can be superimposed on 2D, 3D and/or 4D images of the body of the patient. The images are usually pre-acquired x-ray, computed tomography (CT), ultrasound, and/or magnetic resonance imaging (MRI) images. Superimposing the medical instruments on the images assists a physician or other user in navigating the medical instrument and/or performing a medical procedure.

Although significant improvements have been made in these fields, a need remains for improved medical instruments, systems, and procedures for visualizing, accessing, locating, sampling and manipulating a target tissue.

SUMMARY OF THE INVENTION

One aspect of the invention is directed to medical apparatus and its use, comprising a catheter, a medical instrument assembly, and an imaging assembly. The catheter includes first and second working channels and first and second distal exits, respectively. The medical instrument assembly includes a medical instrument, for example, a needle which is adapted to be housed within the first working channel and is adapted to be extended out the first distal exit to intercept a target tissue proximate an airway of a patient. The imaging assembly includes an imaging device which is adapted to be housed within the first working channel and is adapted to be extended out the second distal exit to generate an image of the medical instrument intercepting the target tissue. The medical instrument is preferably extended through the wall of an airway of a patient from within the airway and the imaging device preferably is extended down an airway branch proximate the target tissue.

Another aspect of the invention is directed to a medical apparatus comprising a catheter, a medical instrument, and an imaging assembly. The catheter comprises a first elongate flexible shaft having a proximal end portion and a distal end portion. The proximal end portion has a first port and a second port, and the distal end portion includes a first distal exit and a second distal exit, wherein a first working channel extends between the first port and the first distal exit, and a second working channel extends between the second port and the second distal exit. The medical instrument assembly includes a medical instrument, wherein the medical instrument has a proximal end and a distal end and is adapted to be housed within the first working channel. The distal end of the medical instrument is extendable through the first distal exit to an extended position beyond the first distal exit. The imaging assembly includes a second elongate flexible shaft having a proximal end portion and a distal end portion, and an imaging device affixed to the distal end portion of the second elongate flexible shaft. The imaging device is adapted to be housed within the second working channel and is extendable through the second distal exit to an extended position beyond the second distal exit. Furthermore, the imaging device is adapted to generate an image in an image plane of the distal end of the medical instrument when the distal end of the medical instrument is extended out the first distal exit.

Another aspect of the invention is directed to a medical apparatus comprising a catheter, a medical instrument assembly, and an imaging assembly. The catheter comprises a first elongate flexible shaft having a proximal end portion, a distal end portion, and a longitudinal axis extending from the proximal end portion to the distal end portion. The proximal end portion has a first port and a second port, and the distal end portion includes a side exit and a distal exit, wherein a first working channel extends between the first port and the side exit, and a second working channel extends between the second port and the distal exit. The medical instrument assembly includes a medical instrument, wherein the medical instrument has a proximal end and a distal end and is adapted to be housed within the first working channel. The distal end of the medical instrument is extendable along a path from a position within the elongate flexible shaft and through the side exit to an extended position outside the elongate flexible shaft at an angle $\Theta$ relative to the longitudinal axis of the first elongate flexible shaft. The imaging assembly includes a second elongate flexible shaft having a proximal end portion and a distal end portion, and an imaging device affixed to the distal end portion of the second elongate flexible shaft. The imaging device is adapted to be translated within the second working channel and is adapted to generate an image in an image plane of the distal end of the medical instrument when the distal end of the medical instrument is extended out the side exit. The imaging plane of the imaging device is adapted to be oriented substantially at the angle $\Theta$ at which the medical instrument extends out the first exit.

Another aspect of the invention is directed to a medical apparatus comprising a catheter and a medical instrument assembly. The catheter comprises a first elongate flexible shaft having a proximal end portion, a distal end portion, and a longitudinal axis extending from the proximal end portion to the distal end portion. The proximal end portion has a port, and the distal end portion includes a side exit, wherein a working channel extends between the port and the side exit. The catheter further includes an imaging device affixed to the distal end portion of the elongate flexible shaft. The imaging device is adapted to generate an image in an image plane of the distal end of the medical instrument when the distal end of the medical instrument is extended out the side exit. The medical instrument assembly includes a medical instrument, wherein the medical instrument has a proximal end and a distal end and is adapted to be housed within the first working channel. The distal end of the medical instrument is extendable along a path from a position within the elongate flexible shaft and through the side exit to an extended position outside the elongate flexible shaft at an angle Θ relative to the longitudinal axis of the first elongate flexible shaft. The imaging plane of the imaging device is oriented substantially at the angle Θ at which the medical instrument extends out the first exit.

Yet another aspect of the invention is directed to a system for intercepting a target tissue proximate an airway of a patient using a medical instrument and generating an image of the medical instrument intercepting the target to provide real-time confirmation of the interception. The system includes a medical apparatus and a navigation system. The medical apparatus comprises a catheter, a medical instrument, and an imaging assembly. The catheter comprises a first elongate flexible shaft having a proximal end portion and a distal end portion. The proximal end portion has a first port and a second port, and the distal end portion includes a first distal exit and a second distal exit, wherein a first working channel extends between the first port and the first distal exit, and a second working channel extends between the second port and the second distal exit. The medical instrument assembly includes a medical instrument, wherein the medical instrument has a proximal end and a distal end and is adapted to be housed within the first working channel. The distal end of the medical instrument is extendable through the first distal exit to an extended position beyond the first distal exit. The imaging assembly includes a second elongate flexible shaft having a proximal end portion and a distal end portion, and an imaging device affixed the distal end portion of the second elongate flexible shaft. The imaging device is adapted to be housed within the second working channel and is extendable through the second distal exit to an extended position beyond the second distal exit. Furthermore, the imaging device is adapted to generate an image in an image plane of the distal end of the medical instrument when the distal end of the medical instrument is extended out the first distal exit. The navigation system includes a processor and a display and is adapted to receive the image(s) generated by the imaging device. The navigation system may display the generated images on the display. In some aspects, the medical instrument assembly, the imaging assembly, and/or the catheter may include localization elements which are adapted to be coupled to the processor and adapted to send to the processor information associated with positions in three-dimensional space of the localization elements.

Yet another aspect of the invention is directed to a system for intercepting a target tissue proximate an airway of a patient using a medical instrument and generating an image of the medical instrument intercepting the target to provide real-time confirmation of the interception. The system includes a medical apparatus and a navigation system. The medical apparatus comprises a catheter, a medical instrument assembly, and an imaging assembly. The catheter comprises a first elongate flexible shaft having a proximal end portion, a distal end portion, and a longitudinal axis extending from the proximal end portion to the distal end portion. The proximal end portion has a first port and a second port, and the distal end portion includes a side exit and a distal exit, wherein a first working channel extends between the first port and the side exit, and a second working channel extends between the second port and the distal exit. The medical instrument assembly includes a medical instrument, wherein the medical instrument has a proximal end and a distal end and is adapted to be housed within the first working channel. The distal end of the medical instrument is extendable along a path from a position within the elongate flexible shaft and through the side exit to an extended position outside the elongate flexible shaft at an angle Θ relative to the longitudinal axis of the first elongate flexible shaft. The imaging assembly includes a second elongate flexible shaft having a proximal end portion and a distal end portion, and an imaging device affixed to the distal end portion of the second elongate flexible shaft. The imaging device is adapted to be translated within the second working channel and is adapted to generate an image in an image plane of the distal end of the medical instrument when the distal end of the medical instrument is extended out the side exit. The imaging plane of the imaging device is adapted to be oriented substantially at the angle Θ at which the medical instrument extends out the first exit. The navigation system may display the generated images on the display. In some aspects, the medical instrument assembly, the imaging assembly, and/or the catheter may include localization elements which are adapted to be coupled to the processor and adapted to send to the processor information associated with positions in three-dimensional space of the localization elements.

Yet another aspect of the invention is directed to a system for intercepting a target tissue proximate an airway of a patient using a medical instrument and generating an image of the medical instrument intercepting the target to provide real-time confirmation of the interception. The system includes a medical apparatus and a navigation system. The medical apparatus comprises a medical instrument assembly and a catheter with an imaging device. The catheter comprises a first elongate flexible shaft having a proximal end portion, a distal end portion, and a longitudinal axis extending from the proximal end portion to the distal end portion. The proximal end portion has a port, and the distal end portion includes a side exit, wherein a working channel extends between the port and the side exit. The catheter further includes an imaging device affixed to the distal end portion of the elongate flexible shaft. The imaging device is adapted to generate an image in an image plane of the distal end of the medical instrument when the distal end of the medical instrument is extended out the side exit. The medical instrument assembly includes a medical instrument, wherein the medical instrument has a proximal end and a distal end and is adapted to be housed within the first working channel. The distal end of the medical instrument is extendable along a path from a position within the elongate flexible shaft and through the side exit to an extended position outside the elongate flexible shaft at an angle Θ relative to the longitudinal axis of the first elongate flexible shaft. The imaging plane of the imaging device is oriented substantially at the angle Θ at which the medical instrument extends out the first exit. The navigation system may display the generated images on the display. In some aspects, the medical instrument assembly, the imaging assembly, and/or the catheter may include localization elements which are adapted to be coupled to the processor and adapted to send to the processor information associated with positions in three-dimensional space of the localization elements.

Yet another aspect of the invention is directed to a method of generating an image of a medical instrument comprising navigating a medical apparatus through an airway of a patient to a position proximate a target, the medical apparatus comprising a catheter, a medical instrument assembly, and an imaging assembly. The catheter comprises an elongate flexible shaft having a proximal end portion and a distal end portion, the proximal end portion comprising a first port and a second port, the distal end portion comprising a first distal exit and a second distal exit, wherein a first working channel extends between the first port and the first distal exit, and a second working channel extends between the second port and the second distal exit. The medical instrument assembly comprises a medical instrument, the medical instrument having a proximal end and a distal end and housed within the first working channel, wherein the distal end of the medical instrument is extendable through the first distal exit to an extended position beyond the first distal exit. The imaging assembly comprises a second elongate flexible shaft having a proximal end portion and a distal end portion, and an imaging device affixed the distal end portion of the second elongate flexible shaft. The imaging device is housed within the second working channel and is extendable through the second distal exit to an extended position beyond the second distal exit. The method continues with extending at least a portion of the medical instrument from within the first working channel out through the first distal exit, extending the imaging device from within the second working channel out through the second distal exit, and generating an image of at least a portion of the medical instrument extended out the first distal exit using the imaging device.

Yet another aspect of the invention is directed to a method of generating an image of a medical instrument comprising navigating a medical apparatus through an airway of a patient to a position proximate a target, the medical apparatus comprising a catheter, a medical instrument assembly, and an imaging assembly. The catheter comprises an elongate flexible shaft having a proximal end portion, a distal end portion, and a longitudinal axis extending from the proximal end portion to the distal end portion. The proximal end portion comprises a first port and a second port and the distal end portion comprises a side exit and a distal exit, wherein a first working channel extends between the first port and the side exit, and a second working channel extends between the second port and the distal exit. The medical instrument assembly comprises a medical instrument, wherein the medical instrument has a proximal end and a distal end and is housed within the first working channel. The distal end of the medical instrument is extendable along a path from a position within the first elongate flexible shaft and through the first exit to an extended position outside the first elongate flexible shaft at an angle Θ relative to the longitudinal axis of the first elongate flexible shaft. The imaging assembly comprises a second elongate flexible shaft having a proximal end portion and a distal end portion, and an imaging device affixed the distal end portion of the second elongate flexible shaft. The imaging device is housed within the second working channel and is adapted to be translated within the second working channel. The method continues with extending at least a portion of the medical instrument from within the first working channel out through the first distal exit, translating the imaging device within the second working channel, and generating an image in an image plane of at least a portion of the medical instrument extended out the first distal exit using the imaging, wherein the imaging plane of the imaging device is oriented substantially at the angle Θ at which the medical instrument extends out the side exit.

BRIEF DESCRIPTION OF THE FIGURES

These and other features, aspects and advantages of the invention will become more fully apparent from the following detailed description, appended claims, and accompanying drawings, wherein the drawings illustrate features in accordance with exemplary embodiments of the invention, and wherein:

FIG. 4AA is a right section view of FIG. 4A showing the attachment of a first localization element to an adjustment handle of the medical instrument assembly according to the first embodiment of the invention;

FIG. 4BB is a right section view of FIG. 4B showing the attachment of a second localization element to an actuation handle of the medical instrument assembly according to the first embodiment of the invention;

FIG. 4CC is a right section view of FIG. 4C showing the optional attachment of a second localization element to a stroke regulator of the medical instrument assembly according to an embodiment of the invention;

FIG. 9 is a flowchart illustrating a method of using the medical apparatus according to the second embodiment of the invention;

Like reference numerals indicate corresponding parts throughout the several views of the various drawings.

DETAILED DESCRIPTION

Figures 1, 1A:
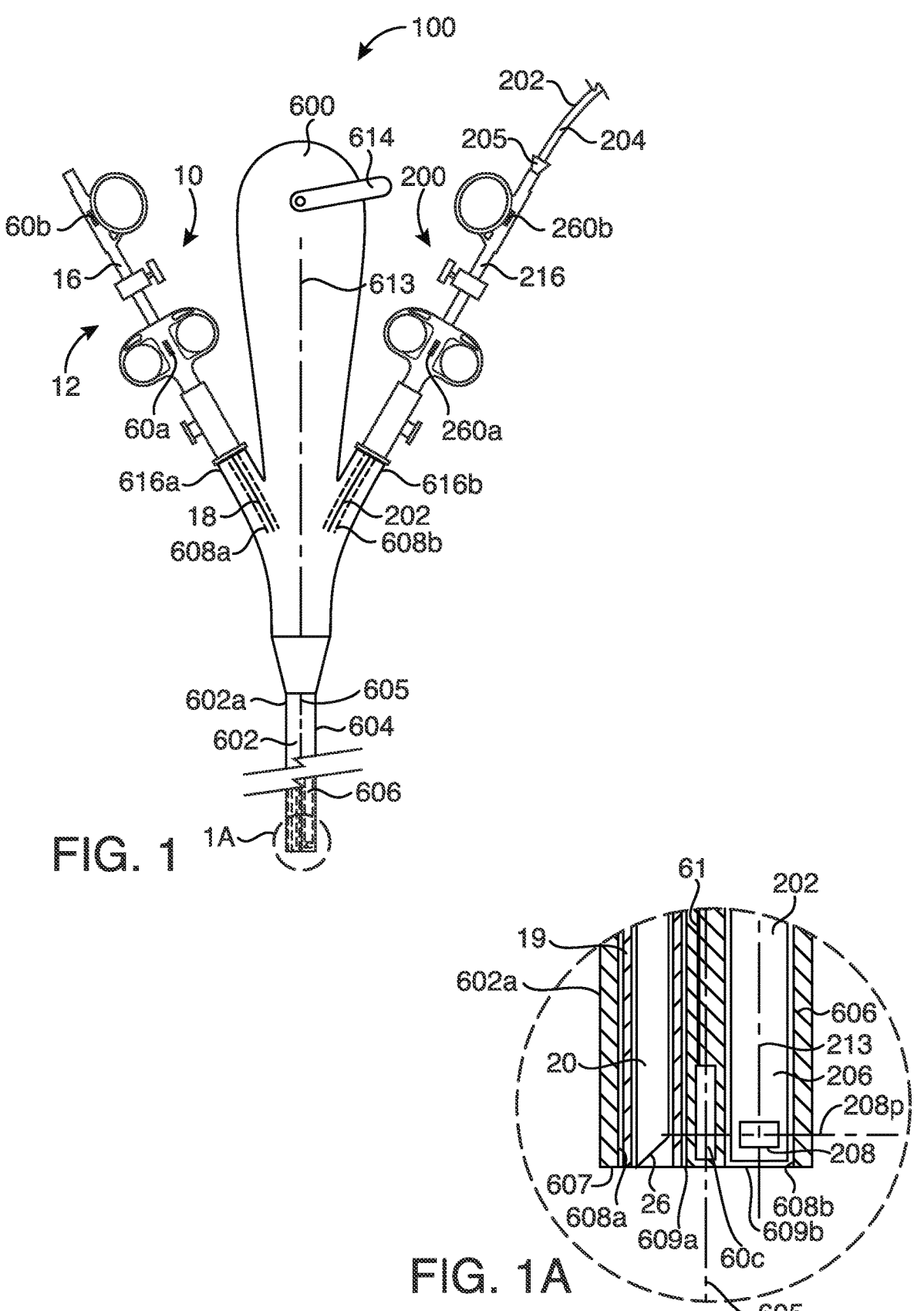
FIG. 1 is a top view of a medical apparatus according to a first embodiment of the invention.
FIG. 1A is a partial section detail view of the medical apparatus according to the first embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. All numbers expressing measurements and so forth used in the specification and claims are to be understood as being modified in all instances by the term "about." It should also be noted that any references herein to front and back, right and left, top and bottom and upper and lower are intended for convenience of description, not to limit an invention disclosed herein or its components to any one positional or spatial orientation.

With larger volumes of patients expected to obtain lung cancer screening, obtaining definitive diagnoses may avoid numerous unneeded lung resections as about only 4% of patients from lung cancer screening are typically found to have a malignancy. However, peripheral target tissues (e.g., nodule, lesion, lymph node, tumor, etc.) that are smaller than 2 cm in size still present a difficult problem to solve. Typical bronchoscopes that are designed mainly for central airway inspection will be limited to the extent they can travel due to their large diameters before becoming wedged in the airway of the patient. Thus, to affect the 5 and 10 year survival rate of patients that have target tissues which may be less than 2 cm in size, the apparatuses and methods as described herein allow for enhanced target tissue interception analysis for staging, obtaining larger and higher quality tissue samples for testing, and provide a streamlined patient flow. In certain patients, portions of the lungs including the upper lobes may move, on average, 15 mm between inspiration and expiration. Using a steerable catheter with an imaging device, such as a radial endobronchial ultrasound (EBUS) transducer inserted therein, a physician or other healthcare professional can determine a confirmed location of the target tissue. Thus it will be understood that the apparatuses and methods described herein may be used to intercept target tissue(s) in the airway, on the wall of the airway, in the wall of the airway, and/or beyond the wall of the airway. That is, the apparatuses and methods described herein may be used to intercept target tissue(s) not only inside the airway, but may intercept target tissue(s) and other anatomical structures inside and/or beyond the wall of the airway. Thus in certain embodiments, sub-surface target tissue(s) may be intercepted.

With reference to FIGS. 1-7B certain principal components of one embodiment of a medical apparatus, system, and method for intercepting a target tissue in a patient and confirming the interception are described in detail. Medical apparatus 100 includes a catheter 600, a medical instrument assembly 10 for intercepting a target tissue, and an imaging assembly 200 for capturing an image of a medical instrument of medical instrument assembly 10 intercepting a target tissue. Intercepting the target tissue may include, but is not limited to, taking a biopsy of the target tissue, treatment of the target tissue, aspiration of the target tissue, delivering therapy or medicine to the target tissue, delivering energy to the target tissue, such as radiation, ablation of the target tissue, etc.

As shown in FIG. 1, catheter 600 is preferably a steerable catheter; however, it will be understood that non-steerable catheters may be used without departing from the scope of the invention. Furthermore, it should be understood that the references made to catheter, mean or include a catheter, an endoscope, and/or a bronchoscope. Accordingly, it will be understood that adjustable length medical instrument 10 may be used with a catheter, an endoscope and/or bronchoscope without departing from the scope of the invention. Steerable catheter 600 comprises an elongate flexible shaft 602 having a proximal end portion 604, a distal end portion 606 terminating in tip 607, and at least two working channels 608a, 608b extending from proximal end portion 604 to distal exits 609a, 609b proximate tip 607. Elongate flexible shaft 602 further includes an outer wall 602a and longitudinal axis 605 extending from proximal end portion 604 to distal end portion 606. Steerable catheter 600 further comprises handle 612 attached to the proximal end portion 604 of elongate flexible shaft 602. Ports 616a, 616b, disposed on handle 612, provide access to working channels 608a, 608b in elongate flexible shaft 602 of steerable catheter 600, such that at least a portion of medical instrument assembly 10 and imaging assembly 200 may be inserted into working channels 608a, 60b through ports 616a, 616b, respectively. Handle 612 of steerable catheter 600 includes steering actuator 614 wherein distal end portion 606 is moved "up" and "down" relative to proximal end portion 604 by manipulating steering actuator 614 "up" and "down," respectively. Additionally, distal end portion 606 is moved "left" and "right" relative to proximal end portion 604 by rotating handle 612 "left" and "right," respectively, about handle longitudinal axis 613. It will be understood that steering actuator 614 and handle 612 are connected to a steering mechanism (not shown) on the inside of steerable catheter 600 which is connected to distal end portion 606 of elongate flexible shaft 602 for causing the deflection in distal end portion 606.

Figures 2, 2A:
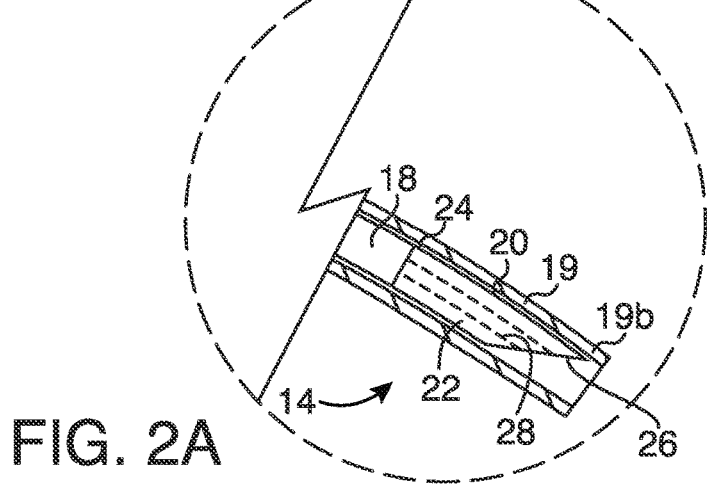
FIG. 2 is a top view of a medical instrument assembly for use with the medical apparatus according to the first embodiment of the invention.
FIG. 2A is a detail view of a medical instrument for use with the medical apparatus according to the first embodiment of the invention.

With reference now to FIGS. 2 and 2A, medical instrument assembly 10 comprises a handle assembly 16 at a proximal end 12 of medical instrument assembly 10, and a medical instrument, preferably needle 20, at the distal end 14 of medical instrument assembly 10. Needle 20 is mechanically coupled to an actuation handle 46 of handle assembly 16, for example, by a flexible guidewire 18. Needle 20 includes an outer wall 22 extending from a proximal end 24 to a tissue piercing distal end 26. Outer wall 22 defines a lumen 28 which extends at least partially from tissue piercing distal end 26 to proximal end 24. Flexible guidewire 18 is attached to proximal end 24 of needle 20. As described in greater detail elsewhere herein, handle assembly 16 includes adjustment collar 38, adjustment handle 40, actuation handle 46, and stroke regulator 48.

Medical instrument assembly 10 may further include a tubular protective sheath 19 having a proximal end 19a attached to and extending from adjustment handle 40 to a distal end 19b proximate tissue piercing distal end 26 of needle 20. Sheath 19 is a tubular structure in which flexible guidewire 18 and needle 20 are housed. Needle 20 is adapted to translate with respect to sheath 19 and may extend out of the open distal end 19b of sheath 19. Sheath 19 serves to cover needle 20 to protect the physician or other user of adjustable medial instrument 10 from accidental pricks by tissue piercing distal end 26 of needle 20.

Needle 20 is adapted to be inserted into working channel 608a of catheter 600. Handle assembly 16 of medical instrument assembly 10 is adapted to be releasably attached to port 616a of catheter 600. As described more fully elsewhere herein, needle 20 is adapted to extend out of catheter 600 to intercept a target tissue. To assist a physician or other user in knowing the actual extension of needle 20, handle assembly 16 is provided with at least two localization elements 60a, 60b whose positions and orientations (POSE) in three-dimensional space can be tracked and compared by a navigation system 70 (see FIG. 6) as will be described more fully elsewhere herein.

As shown in FIG. 2, medical instrument assembly 10 may be an adjustable length medical instrument assembly. Thus, depending on the lengths of flexible guidewire 18, sheath 19, and needle 20 of medical instrument assembly 10 and the length of elongate flexible shaft 602 of steerable catheter 600, distal end 19b of sheath 19, and tissue piercing end 26 of needle 20 may extend past the first exit 609a of steerable catheter 600 when needle 20 should be at the nominal or un-extended position. To account for these length differences and to control the nominal position of distal end 19b of sheath 19 and tissue piercing end 26 of needle 20 within steerable catheter 600, the length of medical instrument assembly 10 can be adjusted by adjusting handle assembly 16. Handle assembly 16 extends from a first end 30 to a second end 32 along longitudinal axis 34. Handle assembly 16 includes adjustment mechanism 36, or first handle portion, proximate first end 30 and actuation handle 46, or second handle portion, proximate second end 32.

Adjustment mechanism 36 is used to control the nominal position of distal end 19b of sheath 19 and tissue piercing end 26 of needle 20 within steerable catheter 600. Specifically, adjustment mechanism 36 includes adjustment collar 38 which is adapted to be releasably connected to first port 616a of steerable catheter 600 and adjustment handle 40 which is slidably engaged with adjustment collar 38. That is, adjustment handle 40 may be translated along longitudinal axis 34 with respect to adjustment collar 38 to control or set the nominal position of sheath 19 and needle 20 within steerable catheter 600. Adjustment handle 40 may include one or more finger holds 41 through which a physician or other user may insert their finger(s) to aid in operation of medical instrument assembly 10. Adjustment collar 38 may include a slot (not shown) along which an adjustment knob 44 affixed to adjustment handle 40 may slide. Adjustment knob 44 is loosened to allow translation of adjustment handle 40 along longitudinal axis 34 with respect to adjustment collar 38. Conversely, adjustment knob 44 is tightened to prevent translation of adjustment handle 40 along longitudinal axis 34 with respect to adjustment collar 38.

While adjustment mechanism 16 controls the nominal position of distal end 19b of sheath 19 and tissue piercing end 26 of needle 20, actuation handle 46 of handle assembly 16 is adapted to extend tissue piercing end 26 of needle 20 past exit 609 of steerable catheter during a medical procedure. Actuation handle 46 may include one or more finger holds 47 through which a physician or other user may insert their finger(s) to aid in extension of tissue piercing distal end 26 of needle 20. Now with reference to FIGS. 2 and 2A, actuation handle 46 is proximate second end 32 of handle assembly 16 and is slidably engaged with adjustment handle 40. That is, actuation handle 46 may be translated along longitudinal axis 34 with respect to adjustment handle 40. Flexible guidewire 18 is attached to actuation handle 46 and serves to mechanically couple needle 20 to actuation handle 46. Therefore, translation of actuation handle 46 with respect to adjustment handle 40 results in a coincident and coextensive translation of flexible guidewire 18 and needle 20 attached thereto. To control the translation (or extension, or stroke) of needle 20 out of exit 609 of steerable catheter 600, a needle extension or stroke regulator 48 (also known as a safety ring) is affixed to actuation handle 46. The movement of actuation handle 46, and therefore any further extension of tissue piercing end 26 of needle 20, is stopped when stroke regulator 48 contacts adjustment handle 40.

With continued reference to FIGS. 2 and 2A, stroke regulator 48 may include a ring 50 which is slidably engaged with actuation handle 46 and adjustment knob 52 on ring 50. Adjustment knob 52 is loosened to allow translation of stroke regulator 48 along longitudinal axis 34 with respect to actuation handle 46. Conversely, adjustment knob 52 is tightened to prevent translation of stroke regulator 48 along longitudinal axis 34 with respect to actuation handle 46. Stroke regulator 48 may be set or secured at a variety of locations on actuation handle 46 along longitudinal axis 34 to regulate or limit the amount of translation (or extension, or stroke) of tissue piercing end 26 of needle 20 out of exit 609 of steerable catheter 600. Stroke regulator 48 may be set to allow from about 0 mm to about 100 mm of extension of needle 20 out of exit 609 of steerable catheter 600 (e.g., about 0 mm, about 10 mm, about 20 mm, about 30 mm, about 40 mm, about 50 mm, about 60 mm, about 80 mm, about 90 mm, about 100 mm). The extension of tissue piercing end 26 of needle 20 is preferably set to a desired "maximum" so that needle 20 will not extend beyond a desired point when in the patient. For example, if the target tissue that a physician or other user wishes to interact with is only 10 mm in diameter, the physician or other user may set the stroke extension of tissue piercing end 26 of needle 20, using stroke regulator 48, to 10 mm so that tissue piercing end 26 of needle 20 does not extend into tissue(s) other than the target. Extension markings (not shown) may be provided on actuation handle 46 to assist in the physician or other user in positioning stroke regulator 48 for the desired extension. While handle assembly 16 is shown as being adjustable, it will be understood that in other embodiments, for example, handle assembly may not have an adjustable length feature without departing from the scope of the invention.

Figure 7:
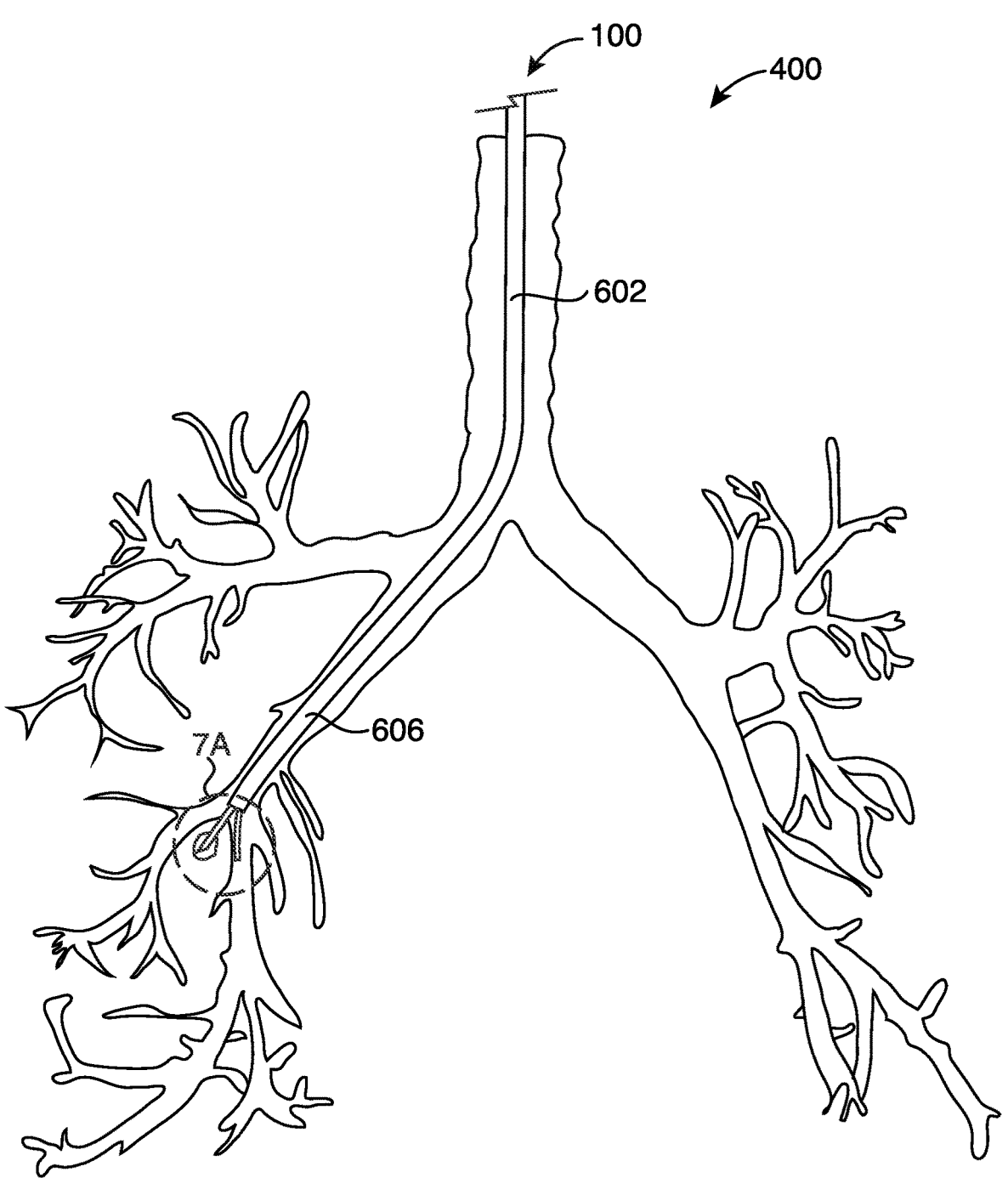
FIG. 7 is a front view of an airway of a patient with the medical apparatus navigated to proximate a target tissue in the patient, wherein a needle is inserted into the target tissue and an imaging device is extended along an airway branch proximate the target tissue to generate an image of the needle intercepting the target tissue according to the first embodiment of the invention.
Figure 7A:
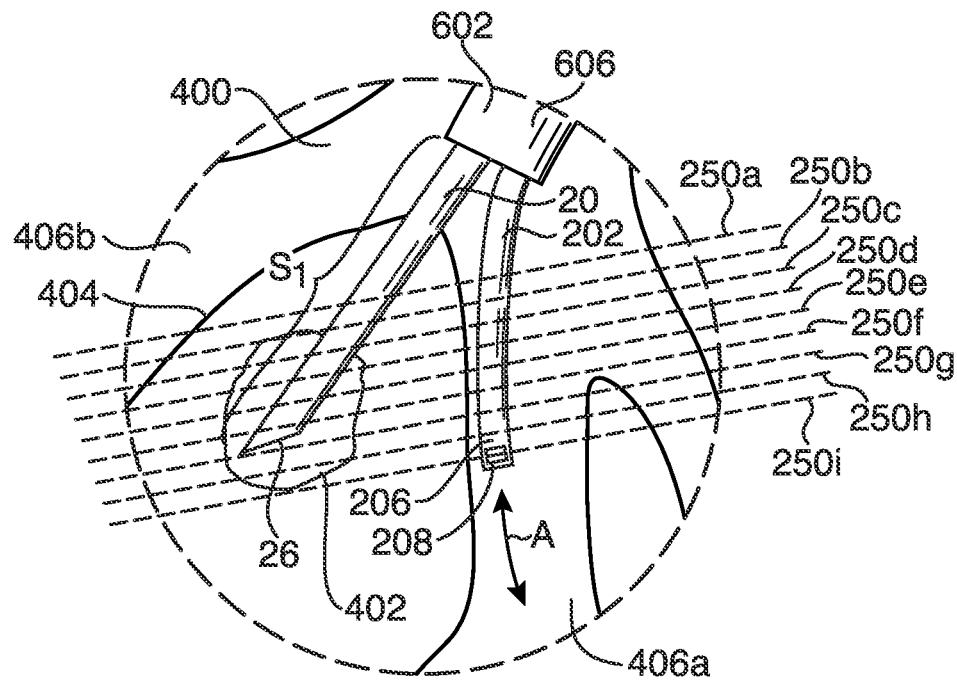
FIG. 7A is a detail front view of an airway of a patient with the medical apparatus navigated to proximate a target tissue in the patient, wherein a needle is inserted into the target tissue and an imaging device is extended along an airway branch proximate the target tissue to generate a population of images of the needle intercepting the target tissue according to the first embodiment of the invention.
Figure 7B:
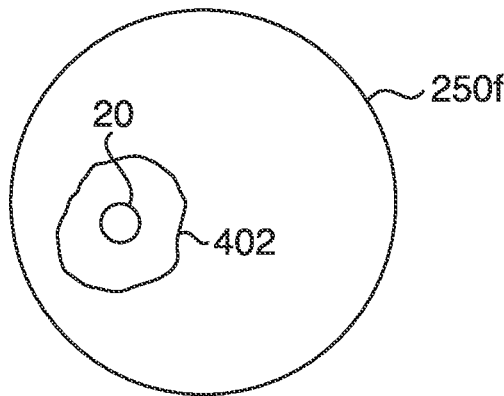
FIG. 7B is a simplified exemplary representation of an image generated by the imaging device of the needle intercepting the target tissue according to the first embodiment of the invention.

Referring again to FIG. 1, imaging assembly 200 comprises an elongate flexible shaft 202 having a proximal end portion 204, a distal end portion 206, and an imaging device 208 affixed to distal end portion 206 of elongate flexible shaft 202. Elongate flexible shaft 202 with imaging device 208 is adapted to be inserted into working channel 608b of catheter 600. Imaging device 208 may generate a population of two-dimensional images in a plane 208p substantially perpendicular to longitudinal axis 213 of elongate flexible shaft 202. The images generated by imaging device 208 are preferably images depicting structures proximate imaging device 208 in plane 208p 360 degrees around longitudinal axis 213. By way of example, FIG. 7B illustrates a simplified image 250c generated by imaging device 208 along image plane 208p depicting needle 20 intercepting target tissue 402. Imaging device 208 is preferably a radial endobronchial ultrasound (EBUS) transducer; however, it will be understood that alternative to a radial EBUS transducer, imaging device 208 may be, but is not limited to, an intravascular ultrasound (IVUS) transducer, an optical coherence tomography (OCT) device, or other type of two-dimensional or three-dimensional imaging device without departing from the scope of the invention. Imaging device 208 may be connected by a wire (not shown) to a navigation system 70 (see FIG. 5) and the generated images may be sent from imaging device 208 to a processor 72 (see FIG. 5) of navigation system 70 and may be displayed on a display 80 (see FIG. 5) of navigation system 70.

Figure 3:
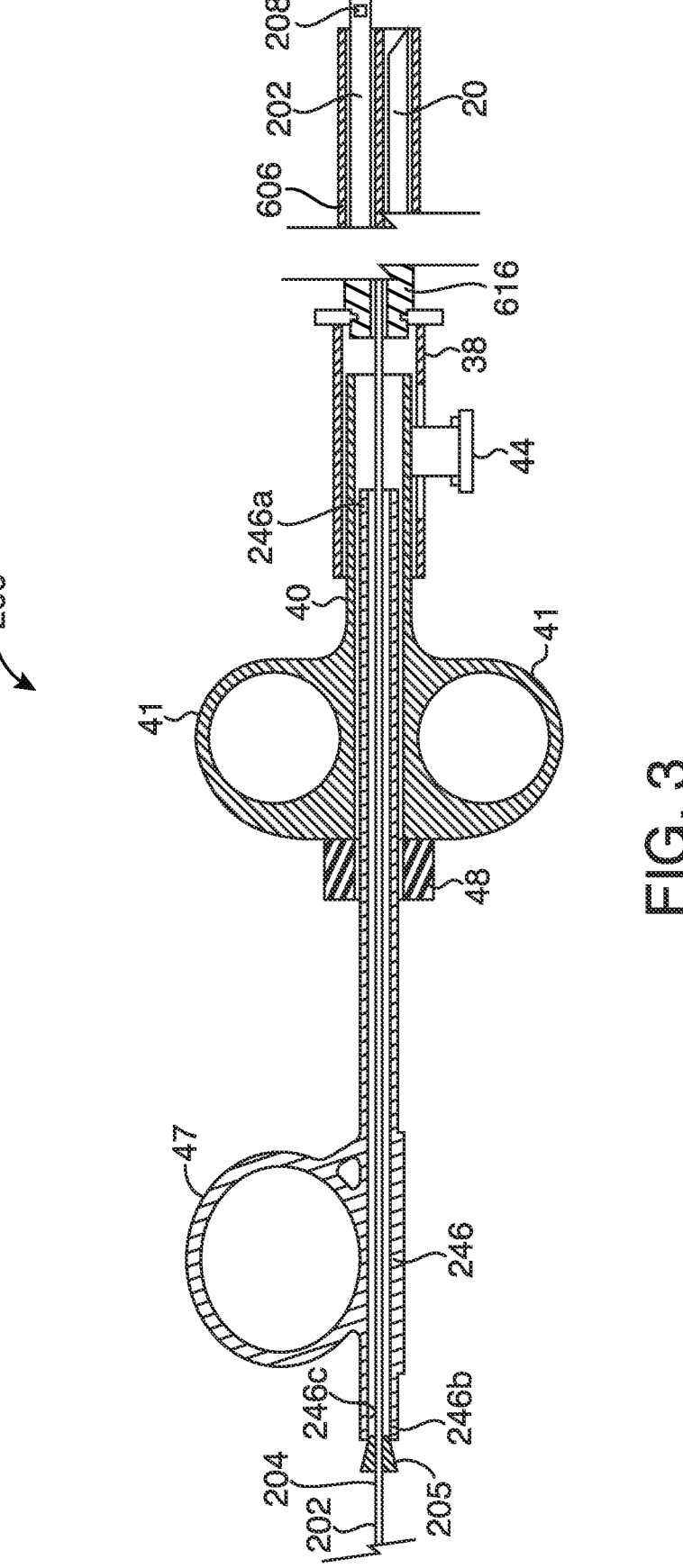
FIG. 3 is a section view of an imaging assembly and a section view of a distal end portion of the imaging assembly inserted into and connected with a catheter, wherein the actuation handle of the imaging assembly is actuated to extend the imaging device according to the first embodiment of the invention.

As shown in greater detail in FIG. 3, imaging assembly 200 further includes handle assembly 216, to which at least a portion of proximal end portion 204 of elongate flexible shaft 202 is mechanically coupled. Various features of handle assembly 216 are common to handle assembly 16 and, accordingly, descriptions of such features with respect to handle assembly 16 should be understood to apply to handle assembly 216. For example, handle assembly 216 may have an adjustable length feature as described with respect to handle assembly 16. Furthermore, particular characteristics and aspects of handle assembly 216 may be used in combination with, or instead of, particular characteristics and aspects of handle assembly 16.

Handle assembly 216 of imaging assembly 200 is adapted to be releasably attached to second port 616b of catheter 600. Actuation handle 246 of handle assembly 216 includes proximal end 246a, distal end 246b, and lumen 246c extending therebetween. Elongate flexible shaft 202 may be inserted through lumen 246c and proximal end portion 204 of elongate flexible shaft 202 may be secured to actuation handle 246 by rubber stopper 205. Rubber stopper 205 assists in preventing translation of elongate flexible shaft 202 with respect to actuation handle 246. Therefore, translation of actuation handle 246 with respect to adjustment handle 40 in the direction of arrow results in a coincident and coextensive translation of elongate flexible shaft 202 attached thereto. By translating actuation handle 246, distal end portion 206 and imaging device 208 are adapted to extend from within second working channel 608b out second exit 609b of catheter 600 to allow imaging device 208 to generate one or more images of needle 20. Preferably, the images depict needle 20 intercepting a target tissue.

It may be also beneficial for the physician or other user to know the extension or stroke of needle 20 out first exit 609a and the extension or stroke of imaging device 208 out second exit 609b of steerable catheter 600. To assist the physician or other user in knowing the extensions of needle 20 and imaging device 208, handle assemblies 16, 216 may be provided with localization elements 60a, 60b and 260a, 260b, respectively, whose positions and orientations (POSE) in three-dimensional space can be tracked and compared by a navigation system 70. In some embodiments, for example, medical instrument assembly 10 and/or imaging assembly 200 may each have only one localization element 60b, 260b affixed to actuation handle 46, 246.

Figure 4A:
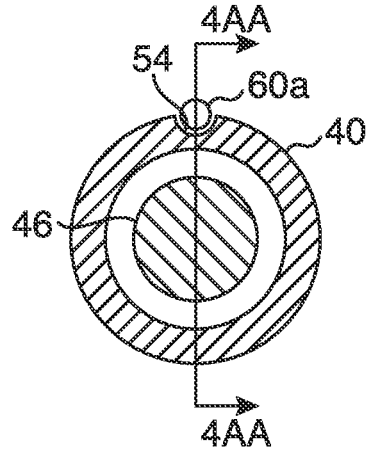
FIG. 4A is a section view of a portion of a medical instrument assembly showing the attachment of a first localization element to an adjustment handle of the medical instrument assembly according to the first embodiment of the invention.
Figure 4A:
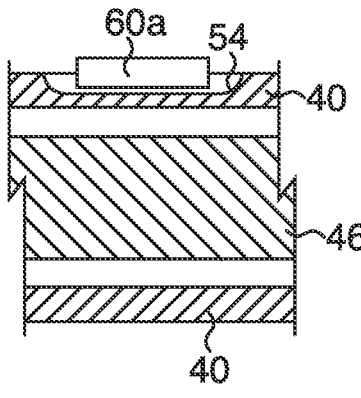
Figure 4B:
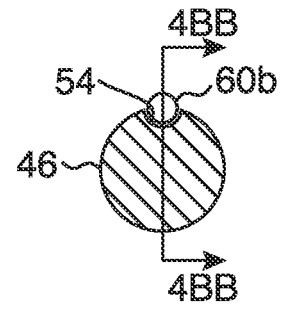
FIG. 4B is a section view of a portion of a medical instrument assembly showing the attachment of a second localization element to an actuation handle of the medical instrument assembly according to the first embodiment of the invention.
Figure 4B:
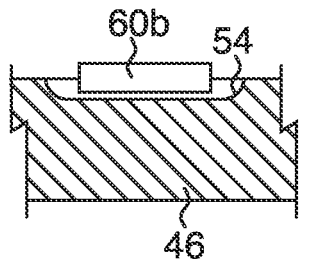
Figure 4C:
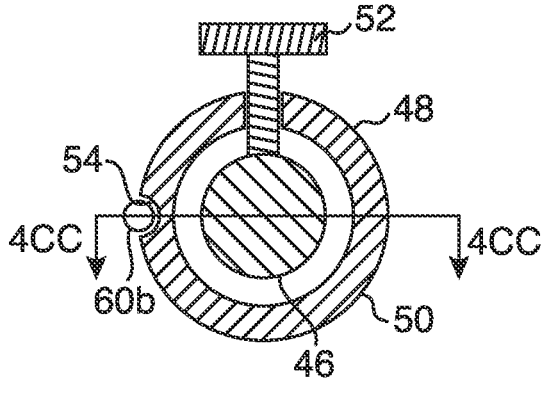
FIG. 4C is a section view of a portion of a medical instrument assembly showing the optional attachment of a second localization element to a stroke regulator of the medical instrument assembly according to an embodiment of the invention.
Figure 4C:
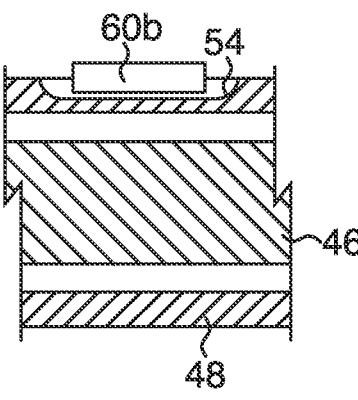

Now with reference to FIGS. 1 and 2 first localization elements 60a, 260a may be affixed or attached to adjustment handles 40 and second localization elements 60b,260b may be affixed to actuation handles 46 and 246, respectively. Preferably, localization elements 60a, 60b, 206a, 260b are releasably affixed or attached to adjustment handles 40 and actuation handles 46, 246. For example, as shown in FIGS. 4A, 4AA, 4B and 4BB, adjustment and actuation handles 40, 46, 246 may have semi-cylindrical slots or grooves 54. Correspondingly, localization elements 60a, 60b, 260a, 260b may be cylindrical in shape and therefore may be snapped or slid into semi-cylindrical slots or grooves 54. While first localization elements 60a, 260a are preferably affixed to adjustment handles 40, it will be understood that, in other embodiments, for example, first localization elements 60a, 260a may be affixed to adjustment collars 38 without departing from the scope of the invention. Additionally, while second localization element 60b is preferably affixed to actuation handle 46, 246 as shown in FIGS. 4A and 4AA, it will be understood that, in other embodiments, for example, second localization element 60b may be affixed to stroke regulator 48 as shown in FIGS. 4C and 4CC without departing from the scope of the invention.

In alternative embodiments, localization elements 60a, 60b, 260a, 260b may be attached to adjustment handle 40, actuation handle 46, 246, adjustment collar 38, and/or stroke regulator 48 by other attachment devices including, but not limited to, adhesives (e.g., tape, glue, cement, etc.), screws, clips, hook-and-loop type fasteners or straps (e.g., Velcro®), bands (e.g., rubber bands, elastic bands, etc.), cable ties, (e.g., zip ties, tie-wrap, etc.), shrink wrap, and any other attachment devices known in the art. While localization elements 60a, 60b, 260a, 20b are preferably releasably affixed to handle assemblies 16, 216, it will be understood that in other embodiments, for example, localization elements 60a, 60b, 260a, 260b may be permanently affixed to handle assemblies 16, 216.

The position and orientation (POSE) of first and second localization elements 60a, 260a and 60b, 260b are detectable by navigation system 70 as described more fully below. The localization elements 60a, 60b, 260a, 260b may be connected by wires (not shown) to navigation system 70; in alternative embodiments, localization elements 60a, 60b, 260a, 260b may be wirelessly connected to navigation system 70. Preferably, localization elements 60a, 60b, 260a, 260b are electromagnetic (EM) coil sensors. In certain embodiments, localization elements 60a, 60b, 260a, 260b are six (6) degree of freedom (6DOF) EM sensors. In other embodiments, localization elements 60a, 60b, 260a, 260b are five (5) degree of freedom (5DOF) EM sensors. In other embodiments, localization elements 60a, 60b, 260a, 260b comprise other localization devices such as radiopaque markers that are visible via fluoroscopic imaging and echogenic patterns that are visible via ultrasonic imaging. In yet other embodiments, localization elements 60a, 60b, 260a, 260b may be, for example, infrared light emitting diodes, and/or optical passive reflective markers. Localization elements 60a, 60b, 260a, 260b may also be, or be integrated with, one or more fiber optic localization (FDL) devices.

Figure 5:
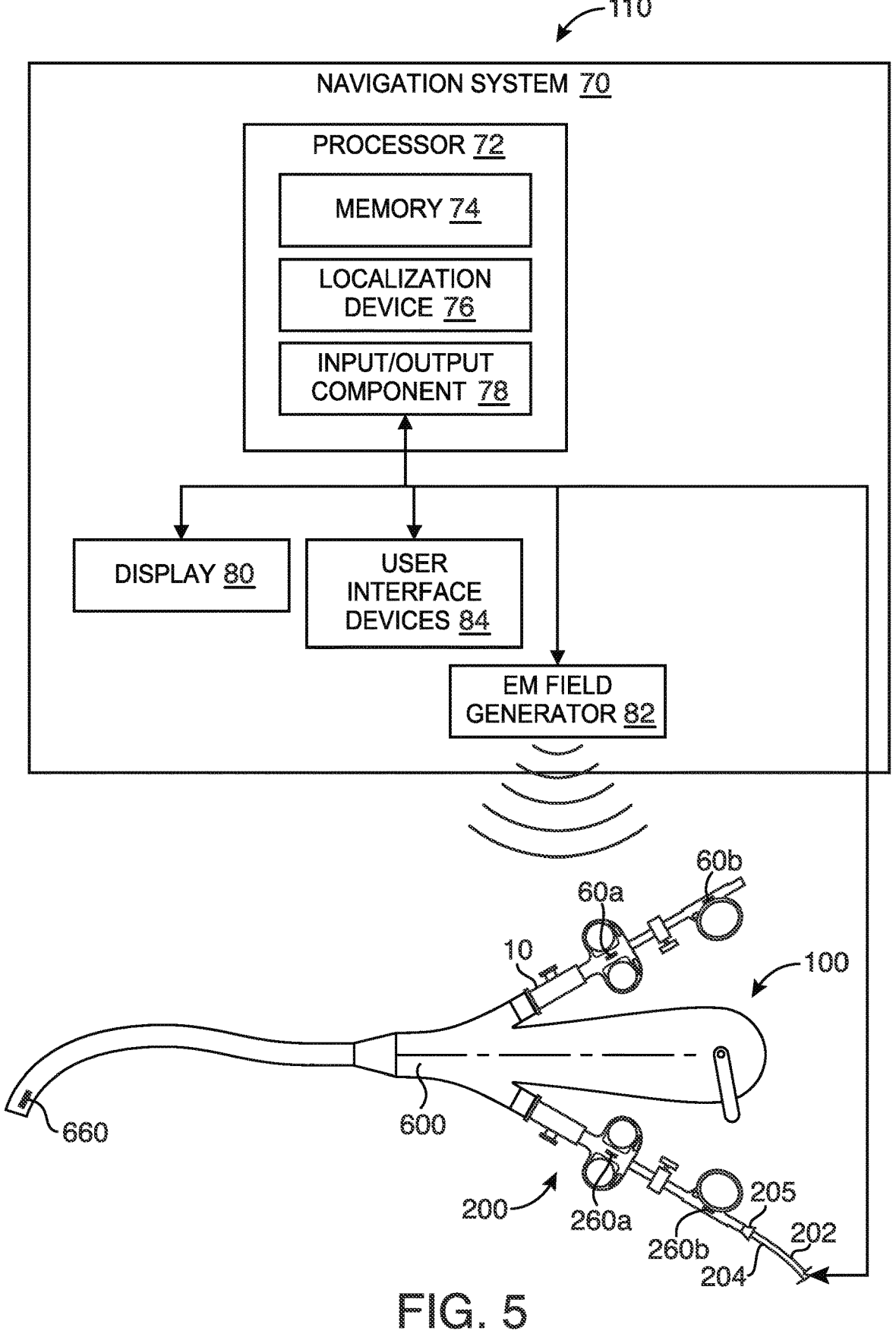
FIG. 5 is a schematic representation of a system comprising the medical apparatus and a navigation system for use with the medical apparatus according to the first embodiment of the invention.
Figure 6:
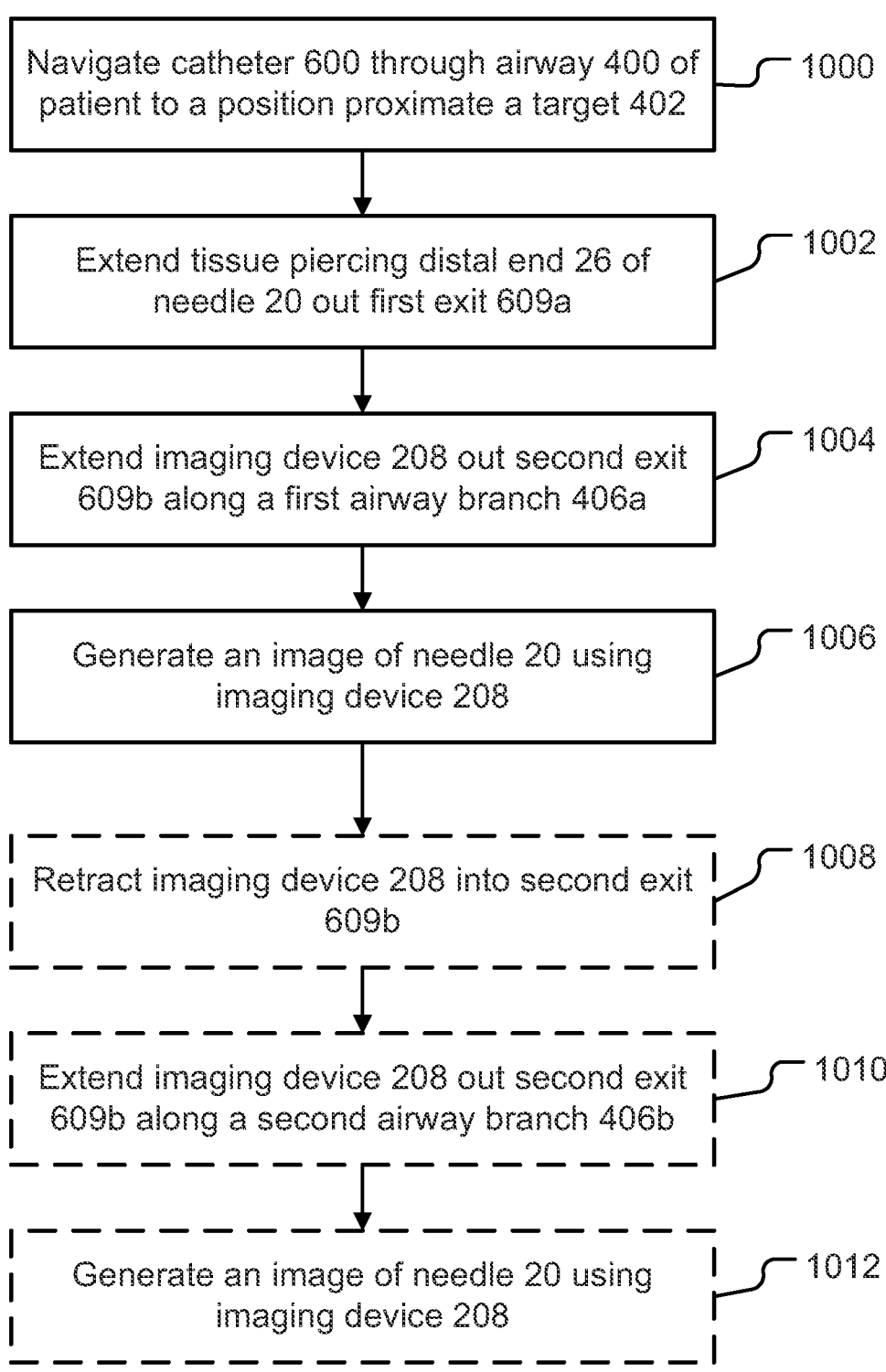
FIG. 6 is a flowchart illustrating a method of using the medical apparatus according to the first embodiment of the invention.

As shown in FIG. 5, system 110 includes medical apparatus 10 and navigation system 70. Navigation system 70 comprises a processor 72 having memory component 74, input/output (I/O) component 78, and localization device 76. Navigation system 70 also includes display 80, electromagnetic field generator 82, and/or user interface device(s) 84 (e.g., keyboard, mouse). Examples of suitable navigation systems are the SPINView® Thoracic Navigation System and the ig4™ M IR System, commercially available from Veran Medical Technologies, Inc. (St. Louis, Missouri USA).

Processor 72 of navigation system 70 includes a processor-readable medium storing code representing instructions to cause the processor 72 to perform a process. Processor 72 can be, for example, a commercially available personal computer, or a less complex computing or processing device that is dedicated to performing one or more specific tasks. For example, processor 72 can be a terminal dedicated to providing an interactive graphical user interface (GUI) on optional display 80. Processor 72, according to one or more embodiments of the invention, can be a commercially available microprocessor. Alternatively, processor 72 can be an application-specific integrated circuit (ASIC) or a combination of ASICs, which are designed to achieve one or more specific functions, or enable one or more specific devices or applications. In yet another embodiment, processor 72 can be an analog or digital circuit, or a combination of multiple circuits.

Additionally, processor 72 can include memory component 74. Memory component 74 can include one or more types of memory. For example, memory component 74 can include a read only memory (ROM) component and a random access memory (RAM) component. Memory component 74 can also include other types of memory that are suitable for storing data in a form retrievable by processor 72. For example, electronically programmable read only memory (EPROM), erasable electronically programmable read only memory (EEPROM), flash memory, as well as other suitable forms of memory can be included within the memory component. Processor 72 can also include a variety of other components, such as for example, coprocessors, graphic processors, etc., depending upon the desired functionality of the code.

Processor 72 can store data in memory component 74 or retrieve data previously stored in memory component 74. The components of processor 72 can communicate with devices external to processor 72 by way of input/output (I/O) component 78. According to one or more embodiments of the invention, I/O component 78 includes a variety of suitable communication interfaces. For example, I/O component 78 can include, for example, wired connections, such as standard serial ports, parallel ports, universal serial bus (USB) ports, S-video ports, local area network (LAN) ports, small computer system interface (SCSI) ports, and so forth. Additionally, I/O component 78 can include, for example, wireless connections, such as infrared ports, optical ports, Bluetooth® wireless ports, wireless LAN ports, or the like. Additionally, display 80, electromagnetic field generator 82, and/or user interface device(s) 84, communicate with processor 72 via I/O component 78.

Processor 72 can be connected to a network, which may be any form of interconnecting network including an intranet, such as a local or wide area network, or an extranet, such as the World Wide Web or the Internet. The network can be physically implemented on a wireless or wired network, on leased or dedicated lines, including a virtual private network (VPN).

In general, navigation system 70 may comprise any tracking system typically employed in image guided surgery, including but not limited to, an electromagnetic tracking system. An example of a suitable electromagnetic tracking subsystem is the AURORA electromagnetic tracking system, commercially available from Northern Digital Inc. (Waterloo, Ontario Canada). In one embodiment, navigation system 70 may include an electromagnetic tracking system, typically comprising an electromagnetic (EM) field generator 82 that emits a series of electromagnetic fields designed to engulf first and second localization elements 60a, 60b, 260a, 260b. In certain embodiments, for example, first and second localization elements 60a, 60b, 260a, 260b are electromagnetic coils that receive an induced voltage from electromagnetic (EM) field generator 82, wherein the induced voltage is monitored and translated by localization device 76 into a coordinate position in three-dimensional space of localization elements 60a, 60b, 260a, 260b. In certain embodiments, localization elements 60a, 60b, 260a, 260b are electrically coupled to twisted pair conductors to provide electromagnetic shielding of the conductors. This shielding prevents voltage induction along the conductors when exposed to the magnetic flux produced by the electromagnetic field generator.

Accordingly, localization device 76 may be, for example, an analog to digital converter that measures voltages induced onto localization elements 60a, 60b, 260a, 260b in the field generated by EM field generator 82; creates a digital voltage reading; and maps that voltage reading to a metric positional measurement based on a characterized volume of voltages to millimeters from electromagnetic field generator 82. Position data associated with localization elements 60a, 60b, 260a, 260b may be transmitted or sent to localization device 76 continuously during a medical procedure. Thus, the position of localization elements 60a, 60b, 260a, 260b may be generated at given instants in time during the medical procedure.

The distance, range, acceleration, and/or speed between first and second localization elements 60a, 60b of medical instrument assembly 10 may then be determined and various algorithms may be used to analyze and compare the distance between first and second localization elements 60a, 60b of medical instrument assembly 10 at given instants in time. Consequently, navigation system 70 may determine the relative distance between first and second localization elements 60a and 60b to determine the actual translation, extension, or stroke ($S_1$, see FIG. 7A) of tissue piercing end 26 of needle 20 out of first exit 609a of steerable catheter 600. Additionally, the distance, range, acceleration, and/or speed between first and second localization elements 260a, 260b of imaging assembly 200 may then be determined and various algorithms may be used to analyze and compare the distance between first and second localization elements 260a, 260b of imaging assembly 200 at given instants in time. Consequently, navigation system 70 may determine the relative distance between first and second localization elements 260a and 260b to determine the actual translation, extension, or stroke of imaging device 208 out of second exit 609b of steerable catheter 600. Additionally, navigation system 70 may determine the location(s) of first and/or second localization elements 260a, 260b when an image is generated by imaging device 208. Navigation system 70 may then determine the distance between each image of the population of images generated by imaging device 208. As described more fully elsewhere herein, processor 72 of navigation system may be able to construct a three-dimensional (3D) image or model from the population of images using the determined distance between the population of images.

To aid in the determination of the actual translation, extension, or stroke (S1) of tissue piercing end 26 of needle 20, the positions of one or both of first localization element 60a and second localization element 60b may be "zeroed out" or initialized prior to any extension of tissue piercing end 26 of needle. For example, after the nominal position of tissue piercing end 26 of needle 20 is set by adjusting adjustable handle 40 with respect to adjustment collar 38 and actuation handle 46 is maintained in a location such that tissue piercing end 26 of needle 20 is not extended, the physician or other user may set on navigation system 70 the positions of one or both of first localization element 60*a* and second localization element 60*b* as initial positions or zero extension positions. This "zeroing out" can be performed to indicate to navigation system 70 that there is no extension of tissue piercing end 26 of needle 20. Accordingly, after zeroing out, relative movement between first and second localization elements 60*a*, 60*b* can indicate the actual translation, extension, or stroke (S₁) of tissue piercing end 26 of needle 20 out of exit 609 of steerable catheter 600. Zeroing out or initialization of the position of first and/or second localization elements 60*a*, 60*b* may be particularly beneficial if first localization element 60*a* is affixed to adjustment collar 38 instead of adjustment handle 40.

The actual translation, extension, or stroke (S₁) of tissue piercing end 26 of needle 20 may be displayed to physician or other user on display 80 of navigation system 70. In various embodiments, the extension or stroke of tissue piercing end 26 of needle 20 may be displayed as a number on display 80. Based on the displayed extension or stroke, the user may then determine whether to continue to extend tissue piercing end 26 of needle 20, to maintain the extension of tissue piercing end 26 of needle 20, or to retract tissue piercing end 26 of needle 20 back into steerable catheter 600.

To provide not only the actual translation, extension, or stroke (S₁) of needle 20 but to also display the trajectory of needle 20, the position and orientation of distal end portion 606 of elongate flexible shaft 602 of steerable catheter 600 may be tracked by navigation system 70. Thus, based on the position and orientations of first and second localization elements 60*a*, 60*b* and the trajectory information of distal end portion 606 of elongate flexible shaft 602, navigation system 70 may be able to display on display 80 a simulated needle extension superimposed on pre-acquired images depicting a portion of the patient including the tissue(s) desired to be targeted by needle 20. Alternatively, navigation system 70 may be able to display on display 80 a simulated needle extension superimposed on a virtual representation of the patient including the tissue(s) desired to be targeted by needle 20. Therefore, the physician or other user may be presented with a real-time simulated display of needle 20 intercepting the target tissue(s).

Having described medical apparatus 10 and system 110 of an embodiment of the invention, the operation and method of use of medical apparatus 10 and system 110 are described in detail with reference to FIGS. 6, 7, 7A, and 7B. At step 1000, a physician or other user navigates distal end portion 606 of catheter 600 through an airway 400 of a patient to a position proximate a target tissue 402 (see FIG. 7). Preferably, medical instrument, such as needle 20, of medical instrument assembly 10 and elongate flexible shaft 202 of imaging assembly 200 are placed into working channels 608*a*, 608*b*, respectively, prior to navigating distal end portion 606 of catheter 600 to the position proximate a target tissue 402. However, it will be understood that in various embodiments, needle 20 of medical instrument assembly 10 and elongate flexible shaft 202 of imaging assembly 200 are placed into working channels 608*a*, 608*b*, respectively, after navigating distal end portion 606 of catheter 600 to the position proximate a target tissue 402.

Following the positioning of distal end portion 606 proximate target tissue 402, at step 1002, tissue piercing distal end 26 of needle 20 is extended from within first working channel 608*a* out first exit 609*a* of catheter 600. As shown in FIGS. 7 and 7A, tissue piercing distal end 26 of needle 20 may be extended through the wall 404 of airway 400 and into tissue 402 located beyond wall 404. Then, at step 1004, with needle 20 still extended, imaging device 208 is extended from within second working channel 608*b* out second exit 609*b* of catheter 600 (see FIG. 7A). Preferably, distal end 206 of elongate flexible shaft 202 is directed down or along a first airway branch 406*a* proximate target 402 (see FIG. 7A).

At step 1006, imaging device 208 generates images of needle 20 extended out exit 609*a*. As shown in FIG. 7A, imaging device 208 may be translated forward and backward along arrows A to generate a population of images 250*a*, 250*b*, 250*c*, 250*d*, 250*e*, 250*f*, 250*g*, 250*h*, 250*i* along image plane 208*p*. By way of example, FIG. 7B illustrates a simplified image 250*f* generated by imaging device 208 along image plane 208*p* depicting needle 20 intercepting target tissue 402. Images 250*a*-250*i* may show target 402 and needle 20 extending into target 20. Imaging device 208 generates images of target 402, needle 20, and other structure beyond wall 404 of airway 400. That is, imaging device 208 can see beyond wall 404. The population of images may be used to confirm that needle 20 actually intercepted the target tissue 402. The population of images generated by imaging device 208 may be sent to processor 72 and may be displayed on display 80 in real time so that a physician or other user can confirm whether or not the needle 20 intercepted the target tissue. These image(s) may also be recorded by processor 72 into a patient file as proof that the target tissue 402 was intercepted. If however, the population of images show that needle 20 did not intercept the target tissue 402, needle 20 and/or imaging device 208 may be retracted into first and second working channels 608*a*, 608*b*, respectively and a subsequent attempt to intercept the target tissue 402 with needle 20 may be made. Imaging device 208 may be extended again and may generate another population of images to confirm that needle 20 intercepted the target tissue 402.

Optionally, after a population of images has be generated by imaging device 208 along first airway branch 406*a*, at step 1008, distal end 206 of elongate flexible shaft 202 of imaging assembly 200 may be retracted into second working channel 608*b* of catheter 600. Preferably with needle 20 still extended, catheter 600 may then be manipulated to place second working channel 608*b* in a position where distal end 206 of elongate flexible shaft 202 and imaging device 208 may be directed down a second airway branch 406*b* proximate target 402. At step 1010, imaging device 208 is extended from within second working channel 608*b* out second exit 609*b* of catheter 600 such that distal end 206 of elongate flexible shaft 202 is directed down second airway branch 406*b* proximate target 402. At step 1012, imaging device 208 then generates a population of images of needle 20 extended out exit 609*a* from an additional point of view as images 250*a*-250*b*. Again, imaging device 208 may be translated forward and backward along second airway branch 406*b* to generate a population of images.

By tracking the positions of first and/or second localization elements 260*a*, 260*b*, navigation system 70 can associate each image of the population of images generated by imaging device 208 with the amount of translation or extension of imaging device 208 at which each image was generated. Based on the amount of translation or extension of imaging device 208, processor 72 of navigation system 70 may construct a three-dimensional (3D) image or volume from the population of images generated by imaging device 208. That is, processor 72 may use the population of images and the position information from first and/or second localization elements 260*a*, 260*b* to produce a three-dimensional (3D) image or model of needle 20 intercepting target tissue 402. This 3D image or model may be shown to physician or user on display 80. This 3D image or model may be enhanced by combining the population of images from both the first and second airway branches 406a, 406b.

Alternative embodiments of apparatuses, systems, and methods of use for intercepting a target tissue in a patient and confirming the interception of a target tissue illustrated in FIGS. 8- and 13B are described below. Some features one or more of apparatuses 100, 2100, and 3100 are common to one another and, accordingly, descriptions of such features in one embodiment should be understood to apply to other embodiments. Furthermore, particular characteristics and aspects of one embodiment may be used in combination with, or instead of, particular characteristics and aspects of another embodiment.

Figures 8, 8A:
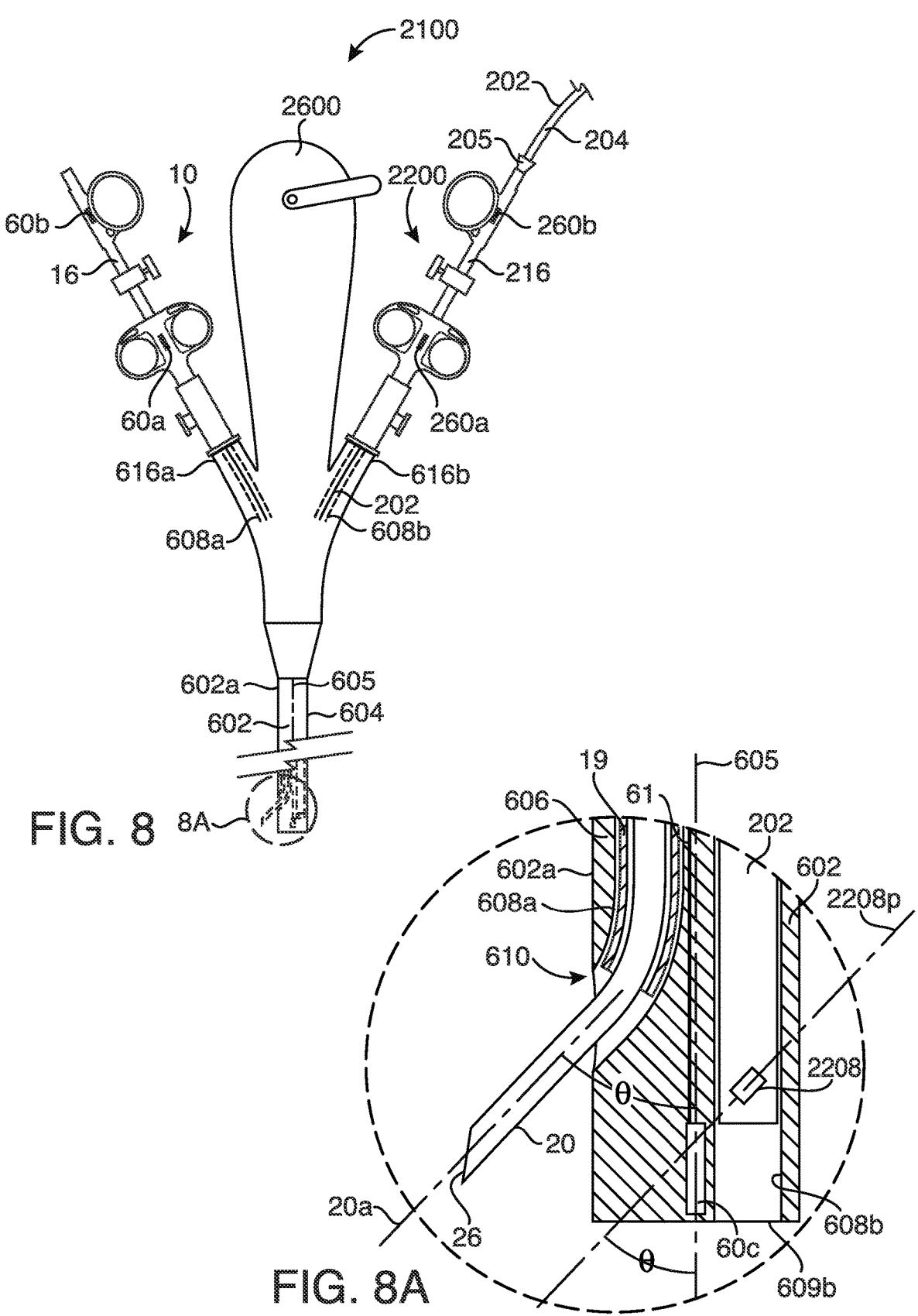
FIG. 8 is a top view of a medical apparatus according to a second embodiment of the invention.
FIG. 8A is a partial section detail view of the medical apparatus according to the second embodiment of the invention.

With reference to FIGS. 8 and 8A, medical apparatus 2100 includes a catheter 2600, a medical instrument assembly 10 for intercepting a target tissue, and an imaging assembly 2200 for capturing an image of a medical instrument of medical instrument assembly 10 intercepting a target tissue.

Catheter 2600 is preferably a steerable catheter; however, it will be understood that non-steerable catheters may be used without departing from the scope of the invention. Steerable catheter 2600 comprises an elongate flexible shaft 602 having a proximal end portion 604, a distal end portion 606 terminating in tip 607, and at least two working channels 608a, 608b extending from proximal end portion 604 to side exit 610 and distal exit 609b proximate tip 607. Elongate flexible shaft 602 further includes an outer wall 602a and longitudinal axis 605 extending from proximal end portion 604 to distal end portion 606. A medical instrument, such as needle 20, can exit side exit 610 at an angle Θ with respect to longitudinal axis 605 and intercept a target to the side of distal end portion 606 of catheter 2600. That is, needle 20 is adapted to exit side exit 610 of catheter 2600 at an angle Θ along axis 20a.

As described above in greater detail, medical instrument assembly 10 comprises a handle assembly 16 at a proximal end 12 of medical instrument assembly 10, and a medical instrument, preferably needle 20, at the distal end 14 of medical instrument assembly 10. Needle 20 is mechanically coupled to an actuation handle 46 of handle assembly 16, for example, by a flexible guidewire 18. Medical instrument assembly 10 also includes protective sheath 19 in which needle 20 and flexible guidewire 18 are housed. Needle 20 is adapted to be inserted into working channel 608a of catheter 2600. Handle assembly 16 of medical instrument assembly 10 is adapted to be releasably attached to port 616a of catheter 2600. To assist a physician or other user in knowing the actual extension of needle 20, handle assembly 16 is provided with localization elements 60a, 60b whose positions and orientations (POSE) in three-dimensional space can be tracked and compared by navigation system 70 (see FIG. 5) as described more fully elsewhere herein.

Figure 10:
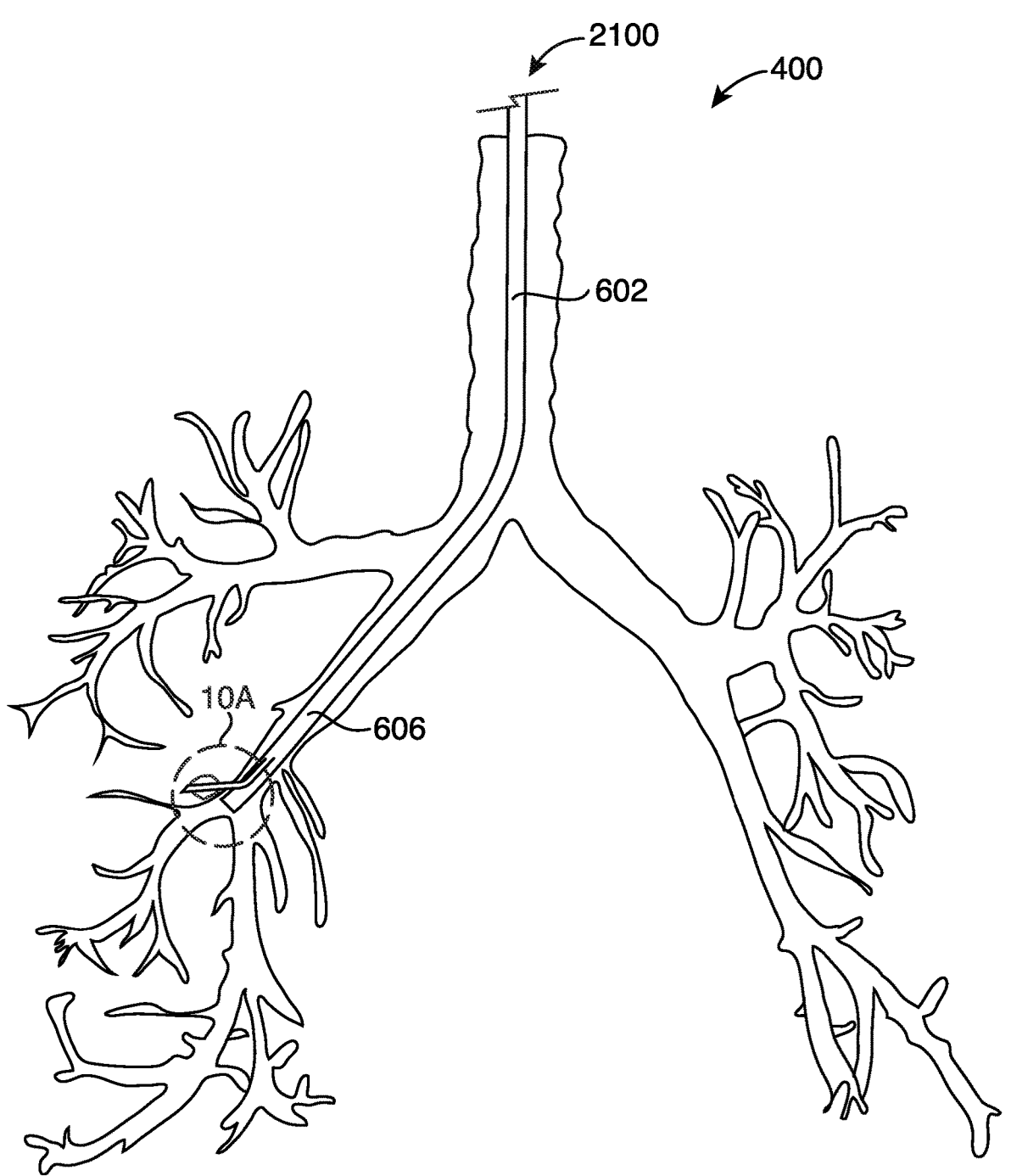
FIG. 10 is a front view of an airway of a patient with the medical apparatus navigated to proximate a target tissue in the patient, wherein a needle is inserted into the target tissue and an imaging device is translated within a catheter to generate an image of the needle intercepting the target tissue according to the second embodiment of the invention.
Figure 10A:
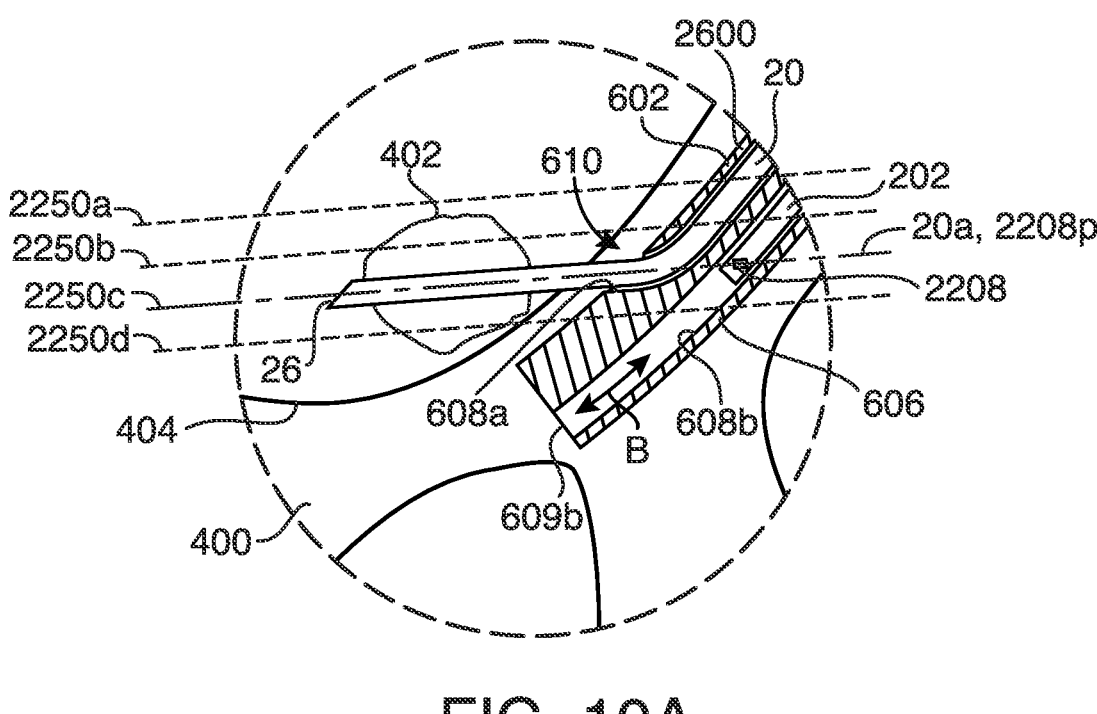
FIG. 10A is a detail front view of an airway of a patient with the medical apparatus navigated to proximate a target tissue in the patient, wherein a needle is inserted into the target tissue and an imaging device is translated within a catheter to generate a population of images of the needle intercepting the target tissue according to the second embodiment of the invention.
Figure 10B:
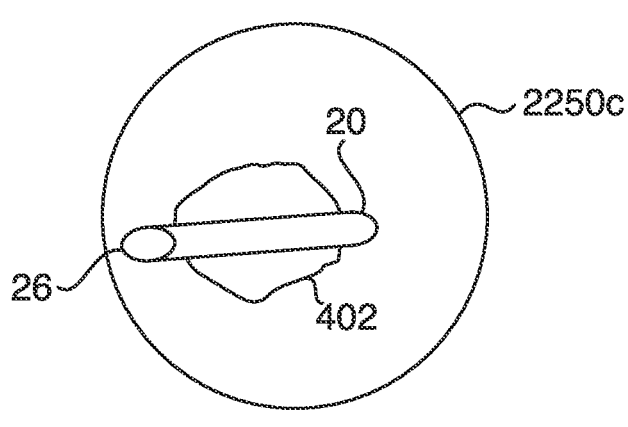
FIG. 10B is a simplified exemplary representation of an image generated by the imaging device of the needle intercepting the target tissue according to the second embodiment of the invention.

Imaging assembly 2200 comprises an elongate flexible shaft 202 having a proximal end portion 204, a distal end portion 206, and an imaging device 2208. Elongate flexible shaft 202 with imaging device 2208 is adapted to be inserted into working channel 608b of catheter 2600. Imaging device 2208 can generate a population of two-dimensional images in a plane 2208p substantially parallel to axis 20a of needle 20 when tissue piercing distal end 26 of needle 20 exits catheter 2600 through side exit 610. Imaging device 2208 is preferably oriented in working channel 608b so that image plane 2208p is at substantially the same angle Θ with respect to longitudinal axis 605 proximate distal end portion 606 at which needle 20 exits side exit 610. The images generated by imaging device 2208 are preferably images depicting structures proximate imaging device 2208 in plane 2208p substantially parallel to axis 20a. The images are preferably a 360 degree view around an axis substantially perpendicular to axis 20a. By way of example, FIG. 10B illustrates a simplified image 2250c generated by imaging device 2208 along image plane 2208p depicting needle 20 intercepting target tissue 402. Because image plane 2208p is substantially parallel to axis 20a, a portion of the length of needle 20 is depicted in image 2250c.

Elongate flexible shaft 202 of imaging device 2208 may be rotatable within second working channel 608b of catheter 2600. Accordingly, in various embodiments, during initial set up of medical apparatus 2100 prior to navigating catheter 2600 through an airway of a patient, elongate flexible shaft 202 of imaging device 2208 may be rotated within second working channel 608b to cause image plane 2208p to be oriented substantially parallel to axis 20a of needle 20. For example, needle 20 may be extended out side exit 610 and a sample image may be generated by imaging device 2208 to check the alignment of image plane 2208p with axis 20a. The rotation of elongate flexible shaft 202 of imaging device 2208 with respect to second working channel 608b may be fixed or substantially fixed prior to navigating catheter 2600 through an airway of the patient. For example, seating rubber stopper 205 in lumen 246b of adjustment handle 246 may be done to reduce or eliminate the rotation of elongate flexible shaft 202. In other embodiments, for example, after distal end portion 606 of catheter 2600 is navigated proximate a target tissue, elongate flexible shaft 202 of imaging device 2208 may be rotated within second working channel 608b to cause image plane 2208p to be oriented substantially parallel to axis 20a of needle 20. After image plane 2208p is aligned with axis 20a of needle 20, subsequent rotation of elongate flexible shaft 202 may be fixed or substantially fixed, for example, by seating rubber stopper 205 in lumen 246b of adjustment handle 246, as described above. In other embodiments, while imaging device 2208 is translated along second working channel 608b and while needle 20 is extended out of side exit 610, elongate flexible shaft 202 of imaging device 2208 may be rotated within second working channel 608b to capture a population of images along image plane 2208p while elongate flexible shaft 202 is rotated. Preferably, by orienting image plane 2208p to be substantially parallel to axis 20a, a single image may show the length of needle 20, including tissue piercing distal end 26, intercepting target tissue 402. This is different from the population of images generated by imaging device 208 described above, wherein a population of images along the length of needle 20 proximate tissue piercing distal end 26 may need to be generated and compiled into a three-dimensional (3D) image or model to show the length of needle 20, including tissue piercing distal end 26, intercepting target tissue 402.

Imaging device 2208 is preferably a radial endobronchial ultrasound (EBUS) transducer; however, it will be understood that alternative to a radial EBUS transducer, imaging device 2208 may be, but is not limited to, an intravascular ultrasound (IVUS) transducer, an optical coherence tomography (OCT) device, or other type of two-dimensional or three-dimensional imaging device without departing from the scope of the invention.

Imaging device 208 may be connected by a wire (not shown) to a navigation system 70 (see FIG. 5) and the generated images may be sent from imaging device 208 to a processor 72 (see FIG. 5) of navigation system 70 and may be displayed on a display 80 (see FIG. 5) of navigation system 70. As described in greater detail elsewhere herein, imaging assembly 2200 further includes handle assembly 216, to which at least a portion of proximal end portion 204 of elongate flexible shaft 202 is mechanically coupled. To assist a physician or other user in knowing the translation of imaging device 2208 and location of images generated by imaging device 2208, handle assembly 216 is provided with localization elements 260a, 260b whose positions and orientations (POSE) in three-dimensional space can be tracked and compared by navigation system 70 (see FIG. 5) as described more fully elsewhere herein. In other embodiments, however, handle assembly 216 may be provided with one localization element affixed to actuation handle 246 without departing from the scope of the invention.

Medical apparatus 2100 combined with navigation system 70 may form a system for intercepting a target tissue and real-time confirming the interception. Having described medical apparatus 2100 and a system of an alternative embodiment of the invention, the operation and method of use of medical apparatus 2100 and the system are described in detail with reference to FIGS. 9, 10, 10A, and 10B. At step 1100, a physician or other user navigates distal end portion 606 of catheter 2600 through an airway 400 of a patient to a position proximate a target tissue 402 (see FIG. 10). Preferably, medical instrument, such as needle 20, of medical instrument assembly 10 and elongate flexible shaft 202 of imaging assembly 2200 are placed into working channels 608a, 608b, respectively, prior to navigating distal end portion 606 of catheter 2600 to the position proximate a target tissue 402. However, it will be understood that in various embodiments, needle 20 of medical instrument assembly 10 and elongate flexible shaft 202 of imaging assembly 2200 are placed into working channels 608a, 608b, respectively, after navigating distal end portion 606 of catheter 2600 to the position proximate a target tissue 402.

Following the positioning of distal end portion 606 proximate target tissue 402, at step 1102, tissue piercing distal end 26 of needle 20 is extended from within first working channel 608a out side exit 610 of catheter 600. As shown in FIGS. 10A and 10B, needle 20 may be extended through the wall 404 of airway 400 and into tissue 402 located beyond wall 404.

At optional step 1104, image plane 2208p of imaging device 2208 may be aligned with axis 20a of needle 20 by rotating elongate flexible shaft 202 of imaging device 2208 within second working channel 608b. This rotation preferably results in image plane 2208p to be oriented substantially parallel to axis 20a of needle 20. As described above, after image plane 2208p is aligned with axis 20a of needle 20, subsequent rotation of elongate flexible shaft 202 may be fixed or substantially fixed, for example, by seating rubber stopper 205 in lumen 246b of adjustment handle 246, at optional step 1106. This serves to maintain the alignment of image plane 2208p with axis 20a.

At steps 1108 and 1110, imaging device 2208 generates images of needle 20 extended out side exit 610. As shown in FIG. 10A, imaging device 2208 may be translated forward and backward along arrows B within second working channel 608b to generate a population of images 2250a, 2250b, 2250c, 2250d. Preferably, an image is generated by imaging device 2208 along an image plane 2208p that is substantially parallel to axis 20a of needle 20. This preferred image is shown as image 2250c in FIGS. 10A and 10B. FIG. 10B illustrates a simplified image generated by imaging device 2208 along image plane 2208p depicting needle 20 intercepting target tissue 402. Because image plane 2208p is substantially parallel to axis 20a, a portion of the length of needle 20 is depicted in image 2250c. Additional images may be generated showing target 402 and/or portions of needle 20 extending into target 20. Imaging device 2208 generates images of target 402, needle 20, and other structure beyond wall 404 of airway 400. That is, imaging device 2208 can see beyond wall 404. The population of images, and specifically image 2250c, may be used to confirm that needle 20 actually intercepted the target tissue 402. Optionally, while imaging device 2208 is translated along second working channel 608b during step 1108 and while needle 20 is extended out of side exit 610, elongate flexible shaft 202 of imaging device 2208 may be rotated within second working channel 608b to capture a population of images along image plane 2208p while elongate flexible shaft 202 is rotated.

The population of images generated by imaging device 2208 may be sent to processor 72 and may be displayed on display 80 in real time so that a physician or other user can confirm whether or not the needle 20 intercepted the target tissue. These image(s) may also be recorded by processor 72 into a patient file as proof that the target tissue 402 was intercepted. If however, the population of images show that needle 20 did not intercept the target tissue 402, needle 20 and/or imaging device 2208 may be retracted into first and second working channels 608a, 608b, respectively and a subsequent attempt to intercept the target tissue 402 with needle 20 may be made. Imaging device 2208 may then generate another population of images to confirm that needle 20 intercepted the target tissue 402.

By tracking the positions of first and second localization elements 260a, 260b, navigation system 70 can associate each image of the population of images generated by imaging device 2208 with the amount of translation or extension of imaging device 2208 at which each image was generated. Based on the amount of translation or extension of imaging device 2208, processor 72 of navigation system 70 may construct a three-dimensional (3D) image or volume from the population of image generated by imaging device 2208. That is, processor 72 may use the population of images and the position information from first and second localization elements 260a, 260b to produce a three-dimensional (3D) image or model of needle 20 intercepting target tissue 402. This 3D image or model may be shown to physician or user on display 80.

With reference to FIGS. 11, 11A, 12, 13, 13A, and 13B, yet another embodiment of an apparatus, system, and method of use for intercepting a target tissue in a patient and confirming the interception of a target tissue is described. Medical apparatus 3100 includes a catheter 3600 and a medical instrument assembly 10 for intercepting a target tissue. Catheter 3600 includes an imaging device 3208 for capturing an image of a medical instrument of medical instrument assembly 10 intercepting a target tissue.

Catheter 3600 is preferably a steerable catheter; however, it will be understood that non-steerable catheters may be used without departing from the scope of the invention. Steerable catheter 3600 comprises an elongate flexible shaft 602 having a proximal end portion 604, a distal end portion 606 terminating in tip 607, and at least one working channel 608 extending from proximal end portion 604 to side exit 610 proximate tip 607. Elongate flexible shaft 602 further includes an outer wall 602a and longitudinal axis 605 extending from proximal end portion 604 to distal end portion 606. A medical instrument, such as needle 20, can exit side exit 610 at an angle Θ with respect to longitudinal axis 605 and intercept a target to the side of distal end portion 606 of catheter 3600. That is, needle 20 is adapted to exit side exit 610 of catheter 3600 at an angle Θ along axis 20*a*.

Figure 13:
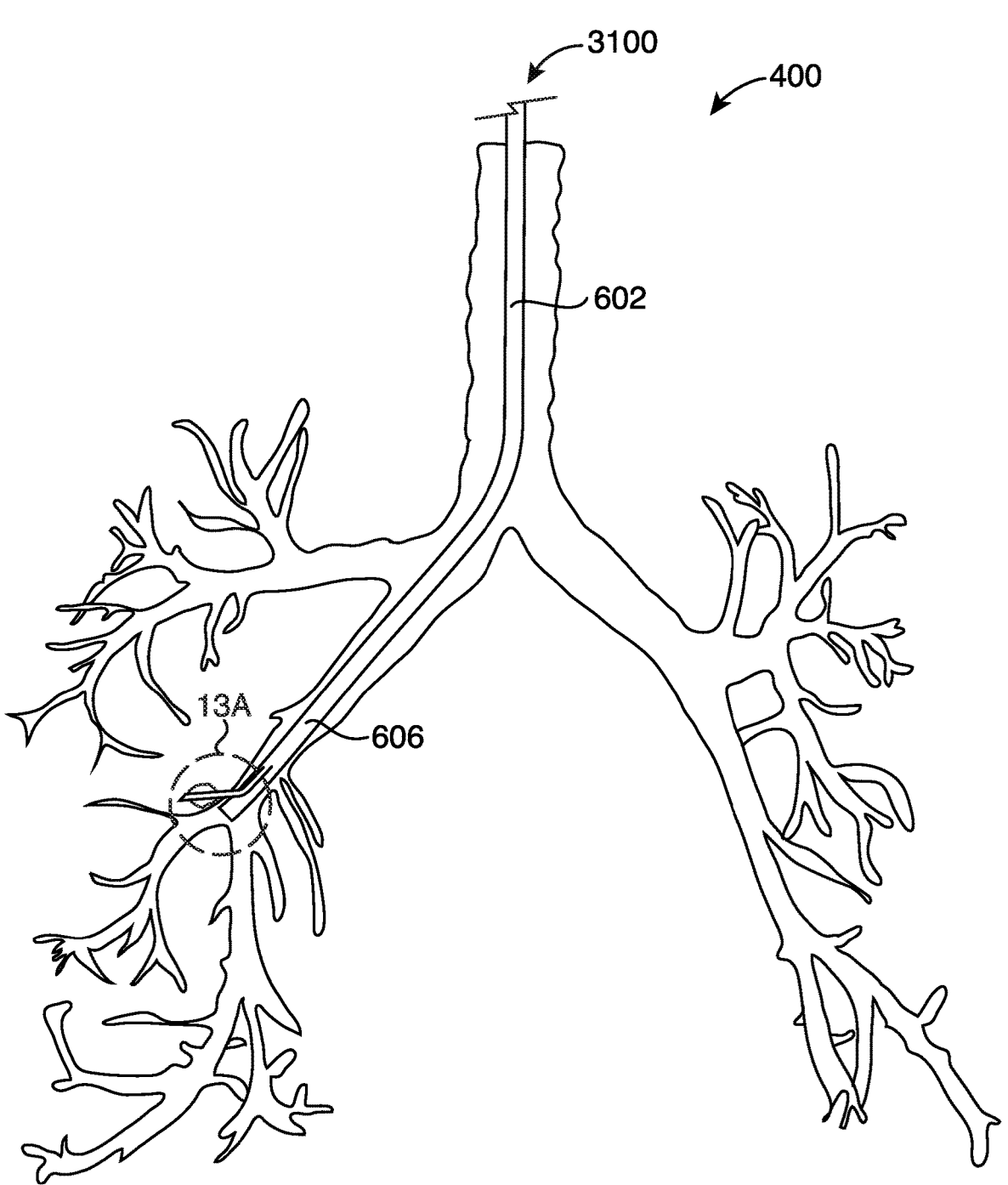
FIG. 13 is a front view of an airway of a patient with the medical apparatus navigated to proximate a target tissue in the patient, wherein a needle is inserted into the target tissue and an imaging device generates an image of the needle intercepting the target tissue according to the third embodiment of the invention.
Figure 13A:
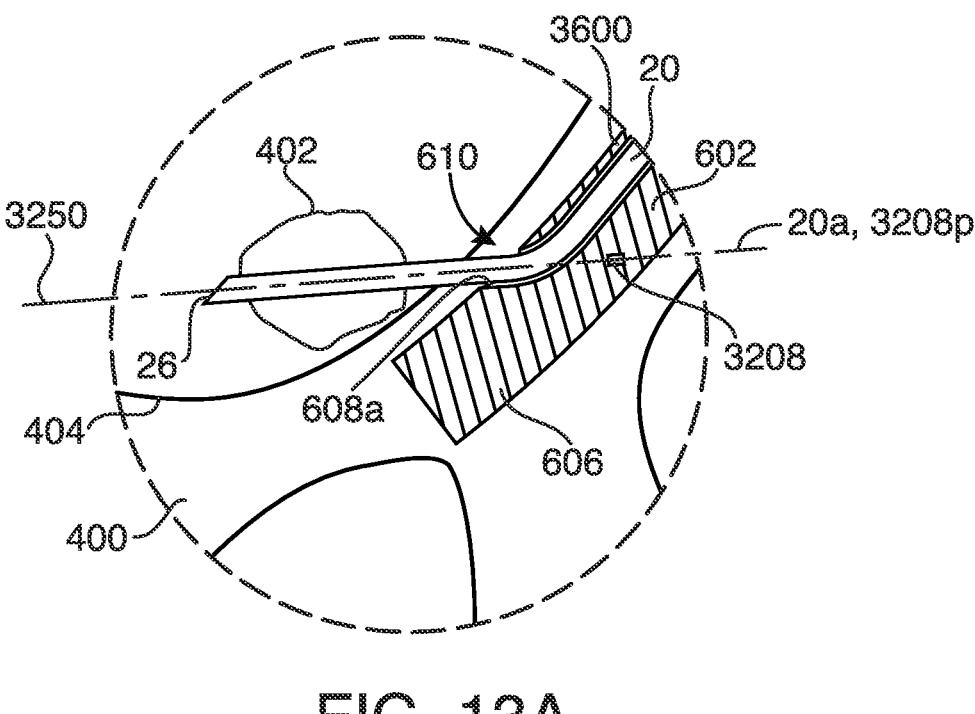
FIG. 13A is a detail front view of an airway of a patient with the medical apparatus navigated to proximate a target tissue in the patient, wherein a needle is inserted into the target tissue and an imaging device generates an image of the needle intercepting the target tissue according to the third embodiment of the invention.
Figure 13B:
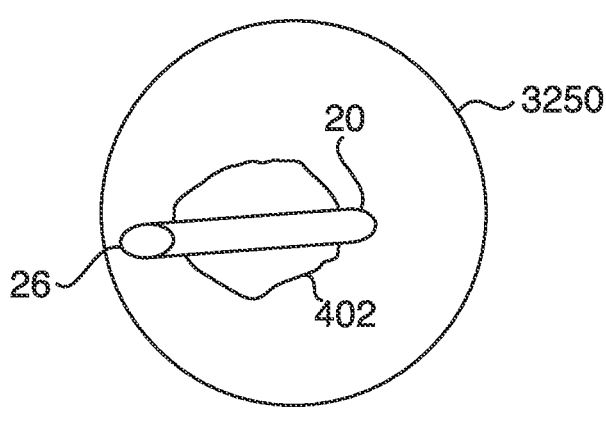
FIG. 13B is a simplified exemplary representation of an image generated by the imaging device of the needle intercepting the target tissue according to the third embodiment of the invention.

Catheter 3600 further includes imaging device 2208 proximate side exit 610 and distal end portion 606 of elongate flexible shaft 602. Imaging device 3208 is preferably oriented in elongate flexible shaft 602 such that images generated by imaging device are in an image plane 3208*p* substantially parallel to axis 20*a* at which needle 20 exits catheter 3600 through exit 610. That is, imaging device 3208 is preferably oriented so that image plane 3208*p* is at substantially the same angle Θ with respect to longitudinal axis 605 proximate distal end portion 606 at which needle 20 exits side exit 610. Additionally, imaging device 3208 is preferably located so that axis 20*a* is in plane with image plane 3208*p*. Thus, imaging device 3208 may generate a population of two-dimensional images in image plane 3208*p* substantially parallel to axis 20*a* of needle 20 when tissue piercing distal end 26 of needle 20 exits catheter 3600 through side exit 610. The images generated by imaging device 3208 are preferably images depicting structures proximate imaging device 3208 in plane 3208*p* substantially parallel to axis 20*a*. The images are preferably a 360 degree view around an axis substantially perpendicular to axis 20*a*. By way of example, FIG. 13B illustrates a simplified image 3250 generated by imaging device 3208 along image plane 3208*p* depicting needle 20 intercepting target tissue 402. Because image plane 3208*p* is substantially parallel to axis 20*a*, a portion of the length of needle 20 is depicted in image 3250. Therefore, by orienting image plane 3208*p* to be substantially parallel to axis 20*a*, a single image may show the length of needle 20, including tissue piercing distal end 26, intercepting target tissue 402. This is different from the population of images generated by imaging device 208 described above, wherein a population of images along the length of needle 20 proximate tissue piercing distal end 26 may need to be generated and compiled into a three-dimensional (3D) image or model to show the length of needle 20, including tissue piercing distal end 26, intercepting target tissue 402.

Imaging device 3208 is preferably a radial endobronchial ultrasound (EBUS) transducer; however, it will be understood that alternative to a radial EBUS transducer, imaging device 3208 may be, but is not limited to, an intravascular ultrasound (IVUS) transducer, an optical coherence tomography (OCT) device, or other type of two-dimensional or three-dimensional imaging device without departing from the scope of the invention. Imaging device 2208 may be connected by a wire (not shown) to a navigation system 70 (see FIG. 5) and the generated images may be sent from imaging device 208 to a processor 72 (see FIG. 5) of navigation system 70 and may be displayed on a display 80 (see FIG. 5) of navigation system 70.

As described above in greater detail, medical instrument assembly 10 comprises a handle assembly 16 at a proximal end 12 of medical instrument assembly 10, and a medical instrument, preferably needle 20, at the distal end 14 of medical instrument assembly 10. Needle 20 is mechanically coupled to an actuation handle 46 of handle assembly 16, for example, by a flexible guidewire 18. Medical instrument assembly 10 also includes protective sheath 19 in which needle 20 and flexible guidewire 18 are housed. Needle 20 is adapted to be inserted into working channel 608 of catheter 3600. Handle assembly 16 of medical instrument assembly 10 is adapted to be releasably attached to port 616 of catheter 3600. To assist a physician or other user in knowing the actual extension of needle 20, handle assembly

16 is provided with at least two localization elements 60*a*, 60*b* whose positions and orientations (POSE) in three-dimensional space can be tracked and compared by navigation system 70 (see FIG. 5) as described more fully elsewhere herein.

Medical apparatus 3100 combined with navigation system 70 may form a system for intercepting a target tissue and real-time confirming the interception. Having described medical apparatus 3100 and a system of an alternative embodiment of the invention, the operation and method of use of medical apparatus 3100 and the system are described in detail with reference to FIGS. 12, 13, 13A and 13B. At step 1200, a physician or other user navigates distal end portion 606 of catheter 3600 through an airway 400 of a patient to a position proximate a target tissue 402 (see FIG. 13). Preferably, medical instrument, such as needle 20, of medical instrument assembly 10 is placed into working channel 608 prior to navigating distal end portion 606 of catheter 3600 to the position proximate a target tissue 402. However, it will be understood that in various embodiments, needle 20 of medical instrument assembly 10 is placed into working channel 608 after navigating distal end portion 606 of catheter 3600 to the position proximate a target tissue 402.

Following the positioning of distal end portion 606 proximate target tissue 402, at step 1202, tissue piercing distal end 26 of needle 20 is extended from within working channel 608 out side exit 610 of catheter 3600. As shown in FIGS. 13 and 13A, needle 20 may be extended through the wall 404 of airway 400 and into tissue 402 located beyond wall 404.

At step 1204, imaging device 3208 generates an image 3250 of needle 20 extended out side exit 610. Image 3250 is generated by imaging device 2208 along an image plane 2208*p* that is substantially parallel to axis 20*a* of needle 20. FIG. 10B illustrates a simplified image 3250 generated by imaging device 3208 along image plane 3208*p* depicting needle 20 intercepting target tissue 402. Because image plane 3208*p* is substantially parallel to axis 20*a*, a portion of the length of needle 20 is depicted in image 3250. Imaging device 3208 generates images of target 402, needle 20, and other structure beyond wall 404 of airway 400. That is, imaging device 3208 can see beyond wall 404. Image 3250 may be used to confirm that needle 20 actually intercepted the target tissue 402. Image 3250 generated by imaging device 3208 may be sent to processor 72 and may be displayed on display 80 in real time so that a physician or other user can confirm whether or not the needle 20 intercepted the target tissue. Image 3250 may also be recorded by processor 72 into a patient file as proof that the target tissue 402 was intercepted. If however, image 3250 show that needle 20 did not intercept the target tissue 402, needle 20 may be retracted into working channel 608 and a subsequent attempt to intercept the target tissue 402 with needle 20 may be made. Imaging device 3208 may generate another image to confirm that needle 20 intercepted the target tissue 402.

Figure 14:
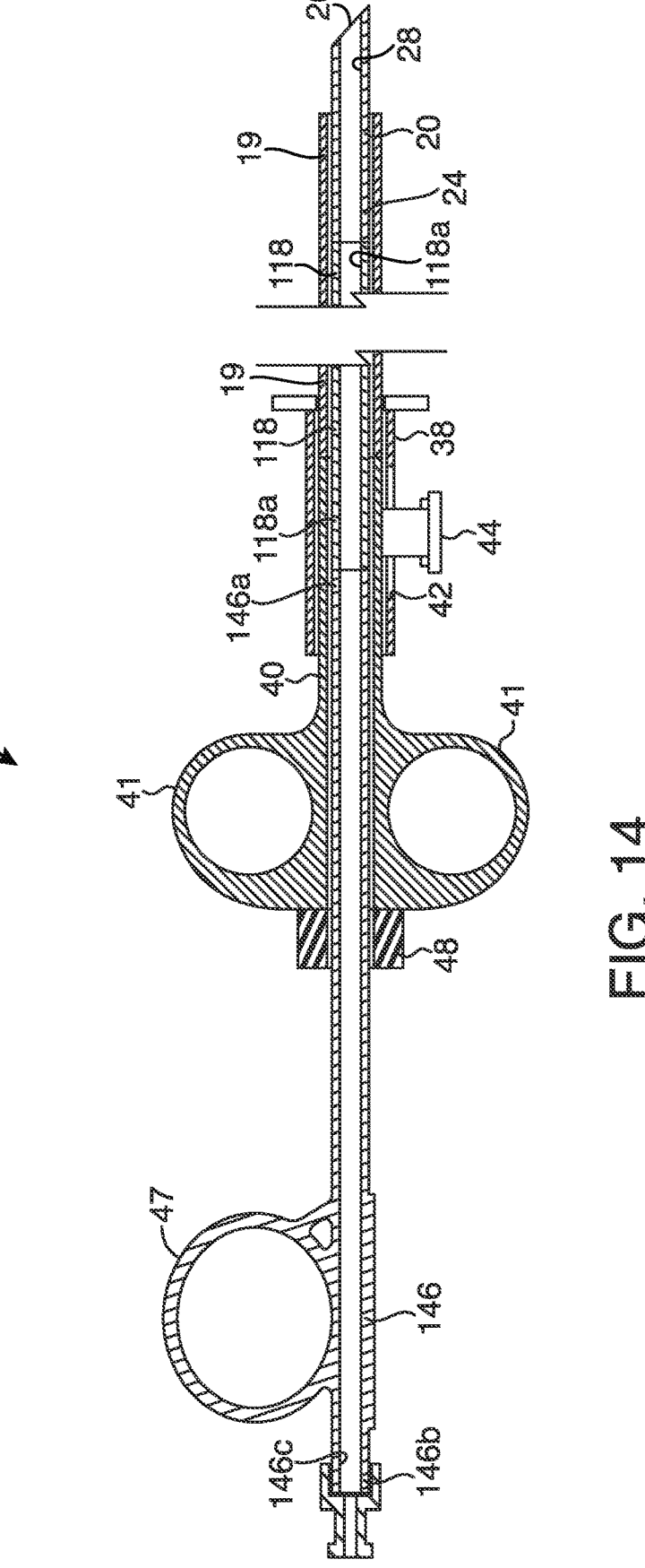
FIG. 14 is a section view of a proximal end portion of a medical instrument assembly and a section view of a distal end portion of the medical instrument assembly, wherein the actuation handle of the medical instrument assembly is actuated to extend the medical instrument according to an embodiment of the invention.
Figure 15:
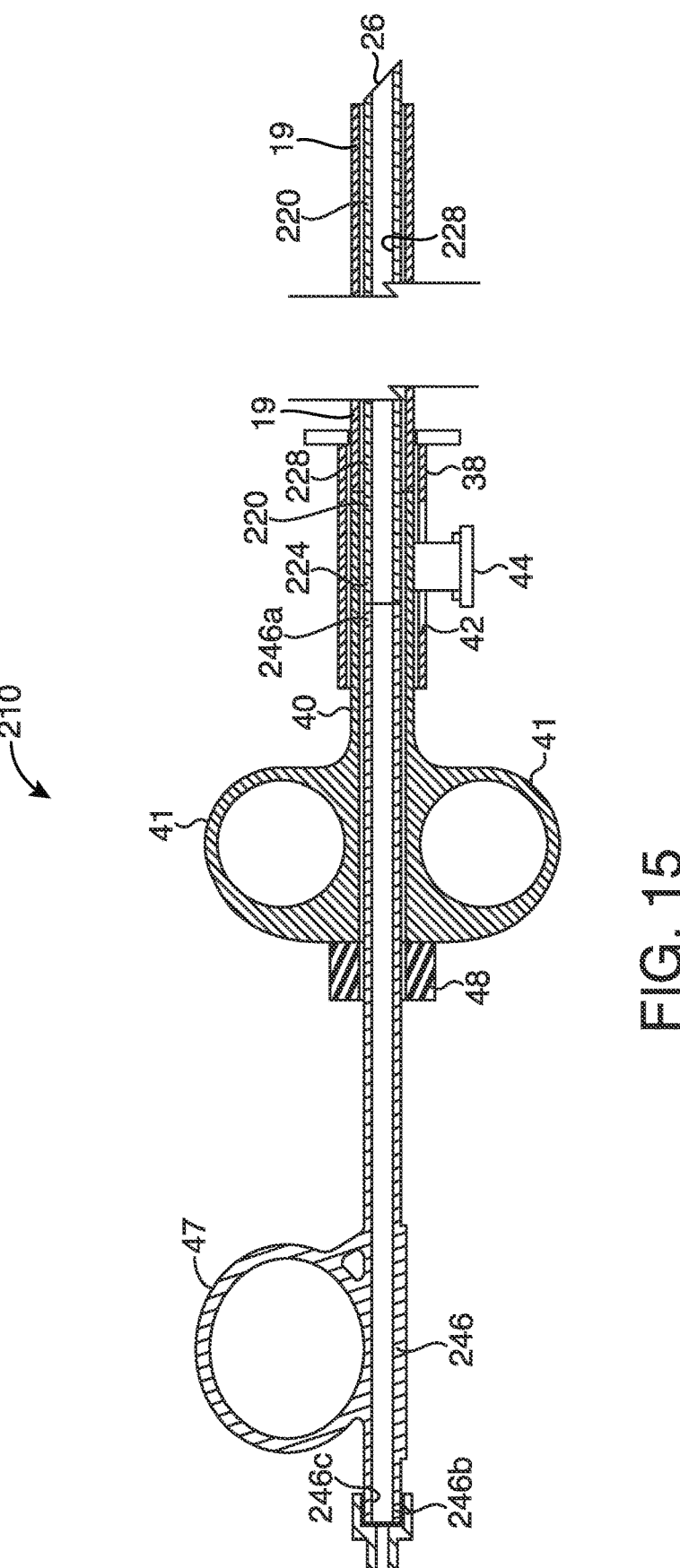
FIG. 15 is a section view of a proximal end portion of a medical instrument assembly and a section view of a distal end portion of the medical instrument assembly, wherein the actuation handle of the medical instrument assembly is actuated to extend the medical instrument according to an embodiment of the invention.

Alternative embodiments of a medical instrument assembly of the disclosure is illustrated in FIGS. 14 and 15 are described below. Some features one or more of medical instrument assembly 10, 110, 210 are common to one another and, accordingly, descriptions of such features in one embodiment should be understood to apply to other embodiments. Furthermore, particular characteristics and aspects of one embodiment may be used in combination with, or instead of, particular characteristics and aspects of another embodiment.

With reference to FIG. 14, actuation handle 146 of medical instrument assembly 110 includes proximal end 146a, distal end 146b, and lumen 146c extending therebetween. Additionally, medical instrument assembly 110 further includes flexible tubing 118 extending from proximal end 146a of actuation handle 146 to proximal end 24 of needle 20. Flexible tubing 118 serves to mechanically couple needle 20 to actuation handle 146. Flexible tubing 118 is preferably hollow, having lumen 118a extending therebetween. Lumen 146c, lumen 118a, and lumen 28 are all in fluid communication with one another which permits material (e.g., tissue, fluid, medicine, devices, etc.) to be passed into or removed out of the patient. As is known in the art, a luer lock fitting or other type of fitting for attaching a syringe may be at distal end 146b of actuation handle to which a syringe may be secured.

With reference to FIG. 15, yet another alternative embodiment of medical instrument assembly 210 is described. Actuation handle 246 of medical instrument assembly 210 includes proximal end 246a, distal end 246b, and lumen 246c extending therebetween. Additionally, medical instrument assembly 210 further includes flexible needle 220 extending from proximal end 246a of actuation handle 246 to tissue piercing distal end 26 of needle 220. That is, instead of the needle being mechanically coupled to the actuation handle by a flexible guidewire or flexible tubing, flexible needle 220 extends from proximate proximal end 12 to distal end 14 of medical instrument assembly 210. Much like flexible tubing 118, flexible needle 220 is preferably hollow, having lumen 228 extending from proximal end 224 of needle 220 affixed to proximal end 246a of actuation handle 246 to tissue piercing distal end 26 of needle 220. Lumen 246c and lumen 228 are in fluid communication with one another which permits material (e.g., tissue, fluid, medicine, devices, etc.) to be passed into or removed out of the patient. As is known in the art, a luer lock fitting or other type of fitting for attaching a syringe may be at distal end 246b of actuation handle to which a syringe may be secured.

Figure 16A:
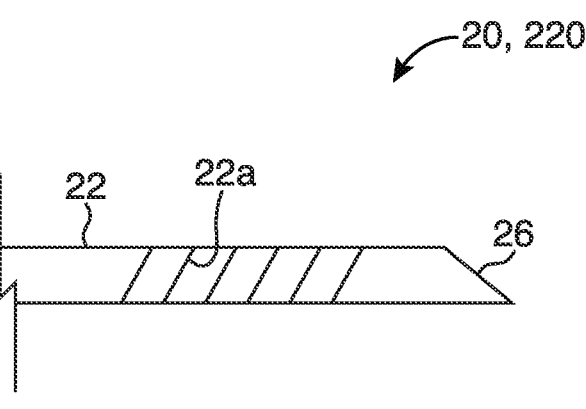
FIG. 16A is a side view of a needle having a population of cuts to increase the flexibility of the needle according to an embodiment of the invention.
Figure 16B:
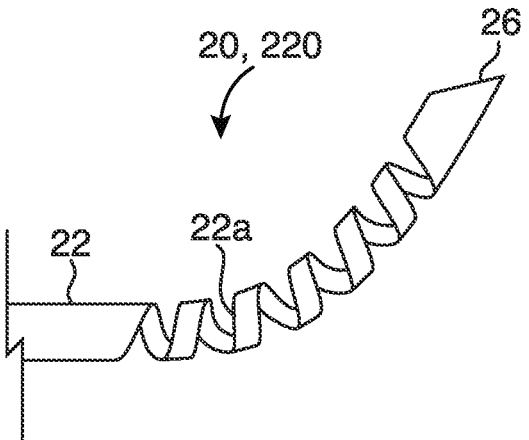
FIG. 16B is a side view showing the needle of FIG. 16A bent according to an embodiment of the invention.

In various embodiments, needle 20, 220 may be highly bendable or flexible. As shown in FIGS. 16A and 16B, needle 20, 220, for example, may include cuts 22a in outer wall 22 to facilitate or increase bending or flexure of needle 20, 220. In various embodiments, for example, cuts may be spiral or helical cuts. In other embodiments, for example, cuts may be in any pattern on outer wall 22 which facilitates or increases bending or flexure of needle 20, 220. Preferably, cuts are made using a laser. In other embodiments, for example, needle 20, 220 may be made or formed of flexible materials including, but not limited to, nitinol, stainless steel, or other metals or alloys thereof, and plastics. Preferably, flexible needle 220 is formed of nitinol.

In various embodiments, with reference to FIGS. 1A, 8A, 11A, 17A, 17B, and 17C, a third localization element 60c may be proximate the tissue piercing distal end 26 of needle 20, 220 to provide trajectory information of needle 20, 220. The position and orientation of the localization element 60c may be tracked by navigation system 70, and may be used in addition to the actual translation, extension, or stroke ($S_1$) of needle 20, 220 to display on display 80 the trajectory of needle 20, 220. Using position and orientation information from localization element 60c, navigation system 70 may display on display 80 a simulated needle extension superimposed on pre-acquired images depicting a portion of the patient including the tissue(s) desired to be targeted by needle 20, 220. Alternatively, navigation system 70 may be able to display on display 80 a simulated needle extension superimposed on a virtual representation of the patient including the tissue(s) desired to be targeted by needle 20, 220. Therefore, the physician or other user may be presented with a real-time simulated display of needle 20 intercepting the target tissue(s).

To determine trajectory information, one or more localization elements 60c that are detectable by a navigation system 70 may be disposed proximate the tissue piercing distal end 26 of needle as shown in 1A, 8A, 11A, 17A, 17B, and 17C. Accordingly, the position and orientation (POSE) of localization elements 60c are tracked by localization device 76 of navigation system 70 and the trajectory of needle 20 may be determined therefrom.

The one or more localization elements 60c may be connected by wire 61 to navigation system 70; in alternative embodiments, the one or more localization elements 60c may be wirelessly connected to navigation system 70. In certain embodiments, localization elements 60c comprise six (6) degree of freedom (6DOF) electromagnetic coil sensors. In other embodiments, localization elements 60c comprise five (5) degree of freedom (5DOF) electromagnetic coil sensors. In other embodiments, localization elements 60c comprise other localization devices such as radiopaque markers that are visible via fluoroscopic imaging and echogenic patterns that are visible via ultrasonic imaging. In yet other embodiments, localization elements 60c may be, for example, infrared light emitting diodes, and/or optical passive reflective markers. Localization elements 60c may also be, or be integrated with, one or more fiber optic localization (FDL) devices.

Figures 11, 11A:
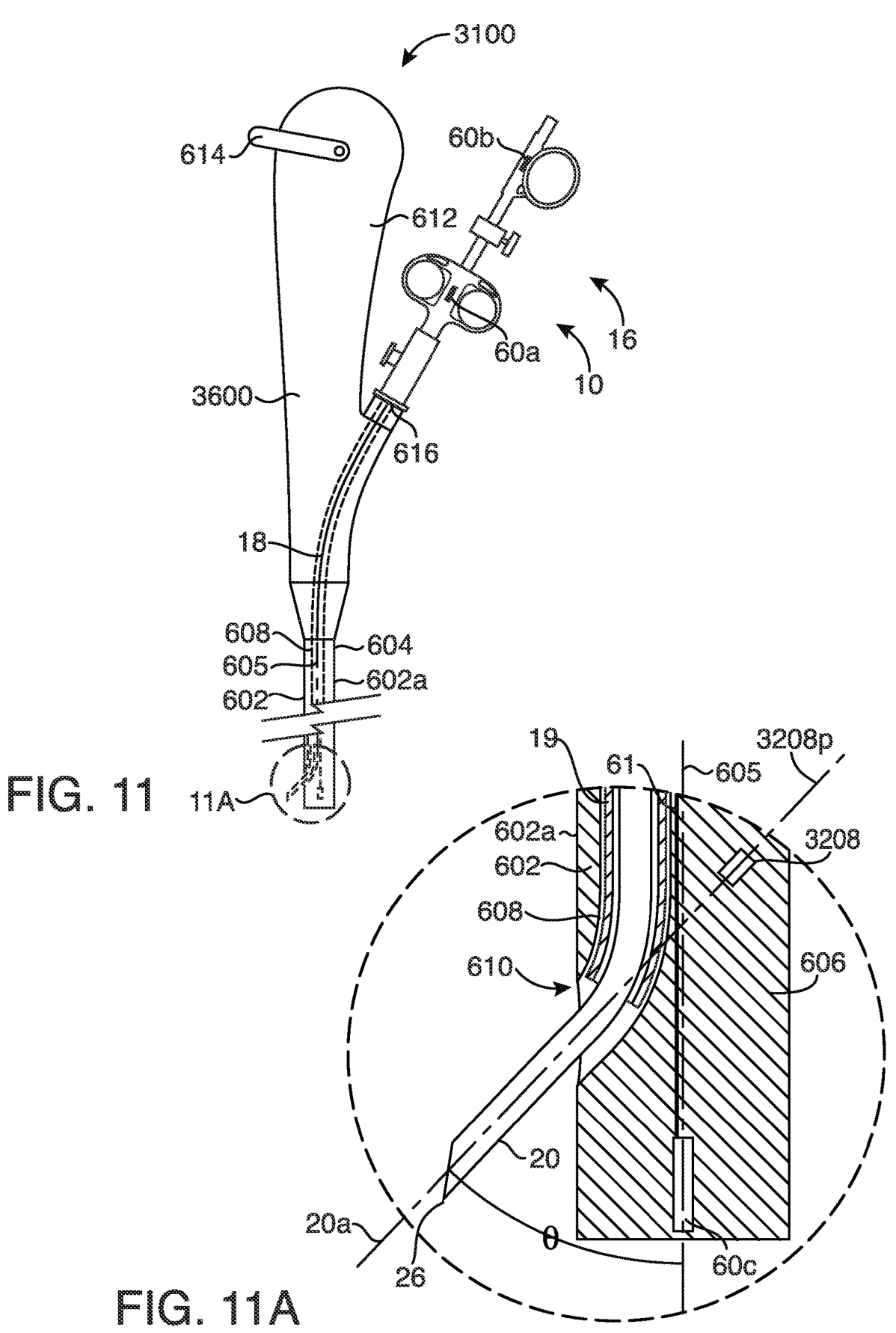
FIG. 11 is a top view of a medical apparatus according to a third embodiment of the invention.
FIG. 11A is a partial section detail view of the medical apparatus according to the third embodiment of the invention.
Figure 12:
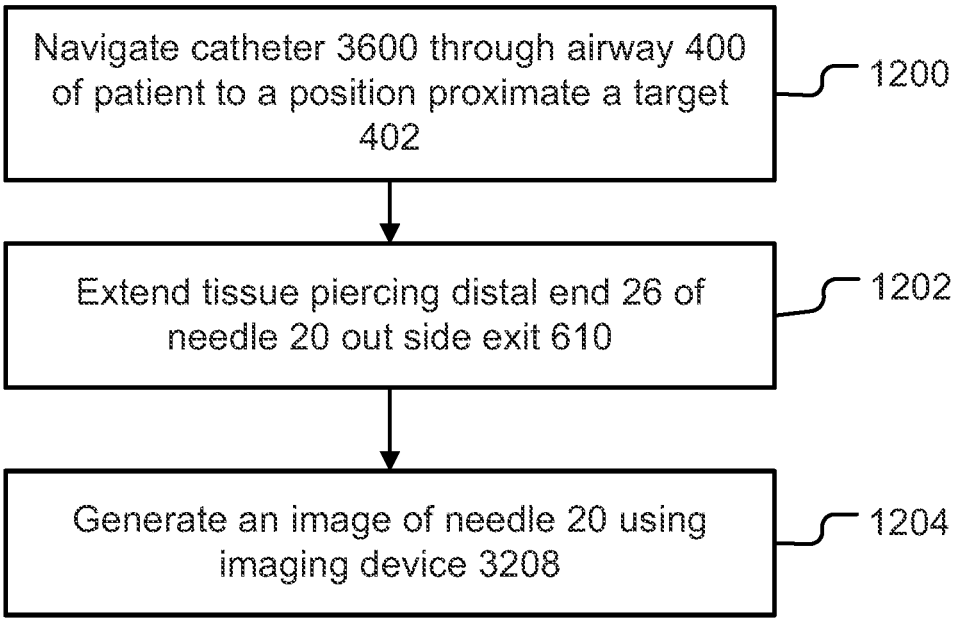
FIG. 12 is a flowchart illustrating a method of using the medical apparatus according to the third embodiment of the invention.
Figure 17A:
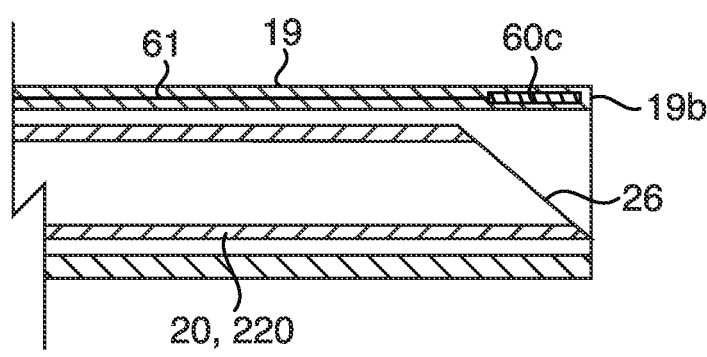
FIG. 17A is a section view of a distal end portion of the medical instrument assembly, having a third localization element on or in the distal end portion of the sheath of the medical instrument assembly according to an embodiment of the invention.
Figure 17B:
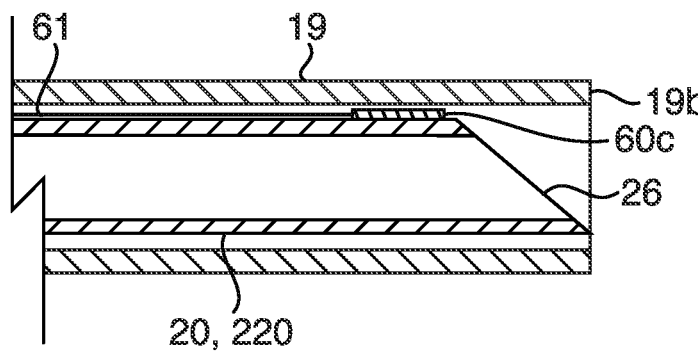
FIG. 17B is a section view of a distal end portion of the medical instrument assembly, having a third localization element on or in the needle of the medical instrument assembly proximate the tissue piercing distal end portion of the needle according to an embodiment of the invention.
Figure 17C:
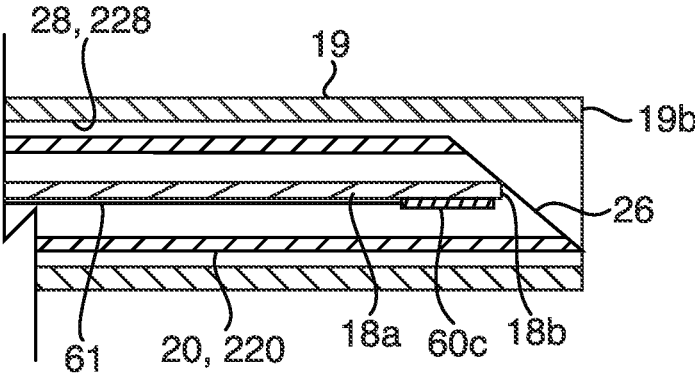
FIG. 17C is a section view of a distal end portion of the medical instrument assembly, having a third localization element on or in a flexible guidewire inserted in a lumen of the needle of the medical instrument assembly according to an embodiment of the invention.

As shown in FIGS. 1A, 8A, and 11A, in various embodiments, for example, localization element 60c is located on or in distal end portion 606 proximate tip 607 of elongate flexible shaft 602 of catheter 600, 2600, 3600. In other embodiments, for example, as shown in FIG. 17A, localization element 60c is located on or in distal end 19b of sheath 19 of medical instrument 10, 110, 210. As shown in FIG. 17B, in yet other embodiments, for example, localization element 60c is located on or in needle 20, 220 proximate tissue piercing distal end 26. In yet other embodiments, for example, as shown in FIG. 17C, localization element 60c is located on or in the tip 18b of flexible guidewire 18a which may be inserted through lumen 146c of actuation handle 146 and lumen 118a of flexible tubing 118 of medical instrument 110 to proximate tissue piercing distal end 26 of needle 20 or through lumen 246c of actuation handle 246 and lumen 228 of needle 220 of medical instrument 210 to proximate tissue piercing distal end 26 of needle 220. In various embodiments, localization element 60c may be integrally formed with elongate flexible shaft 602 of catheter, sheath 19, needle 20, 220, and/or flexible guidewire 18a. In other embodiments, localization element 60c may be affixed or adhered to elongate flexible shaft 602 of catheter 600, 2600, 3600, sheath 19, needle 20, 220, and/or flexible guidewire 18a. For example, localization element 60c may be affixed to needle 20, 220 by a length of heat skink tubing. In other embodiments, localization element 60c may be affixed or adhered to elongate flexible shaft 602 of catheter 600, 2600, 3600, sheath 19, needle 20, 220, and/or flexible guidewire 18a by any type of bio-compatible adhesives and/or tapes known in the art. By including localization element 60c on sheath 19, needle 20, 220, and/or on flexible guidewire 18a, catheter 600, 2600, 3600 may be a cheaper non-navigated catheter.

Figures 18A, 18B, 18C:
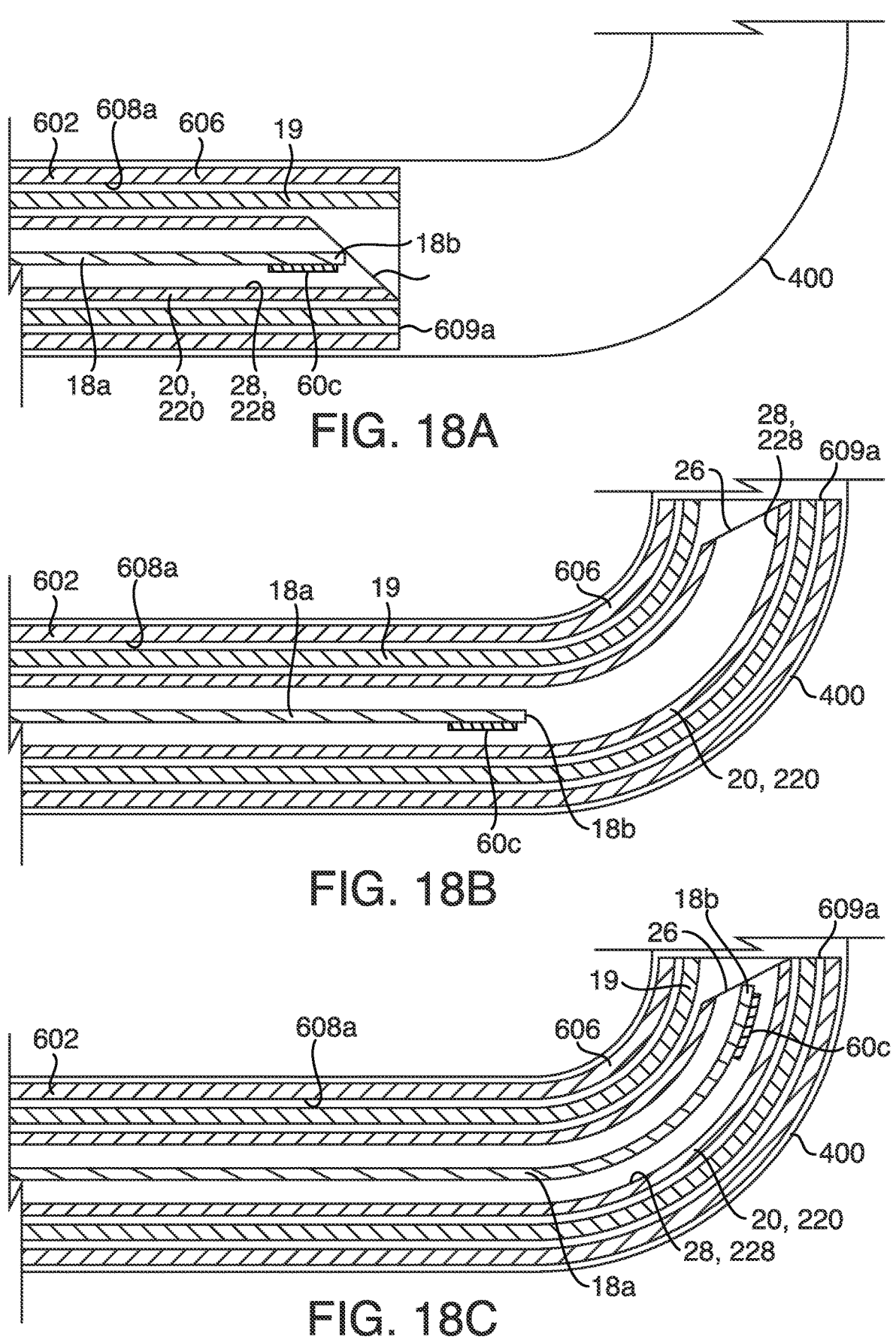
FIG. 18A is a section view of a distal end portion of the medical instrument assembly and the distal end portion of the elongate flexible shaft of the catheter, wherein a third localization element is on or in a flexible guidewire inserted in a lumen of the needle of the medical instrument assembly, wherein the distal end of the flexible guidewire is proximate the tissue piercing distal end portion of the needle as the catheter is being navigated in an airway according to the embodiment of the invention shown in FIG. 17C.
FIG. 18B is a section view of a distal end portion of the adjustable length medical instrument assembly and the distal end portion of the elongate flexible shaft of the catheter, wherein a third localization element is on or in a flexible guidewire inserted in a lumen of the needle of the adjustable length medical instrument assembly, wherein the distal end of the flexible guidewire is partially retracted from the tissue piercing distal end portion of the needle as the catheter is being navigated in an airway according to the embodiment of the invention shown in FIG. 17C.
FIG. 18C is a section view of an end portion of the adjustable length medical instrument assembly and the distal end portion of the elongate flexible shaft of the catheter, wherein a third localization element is on or in a flexible guidewire inserted in a lumen of the needle of the adjustable length medical instrument assembly, wherein the distal end of the flexible guidewire is proximate the tissue piercing distal end portion of the needle as catheter is being navigated in an airway according to the embodiment of the invention shown in FIG. 17C.
Figures 19A, 19B, 19C:
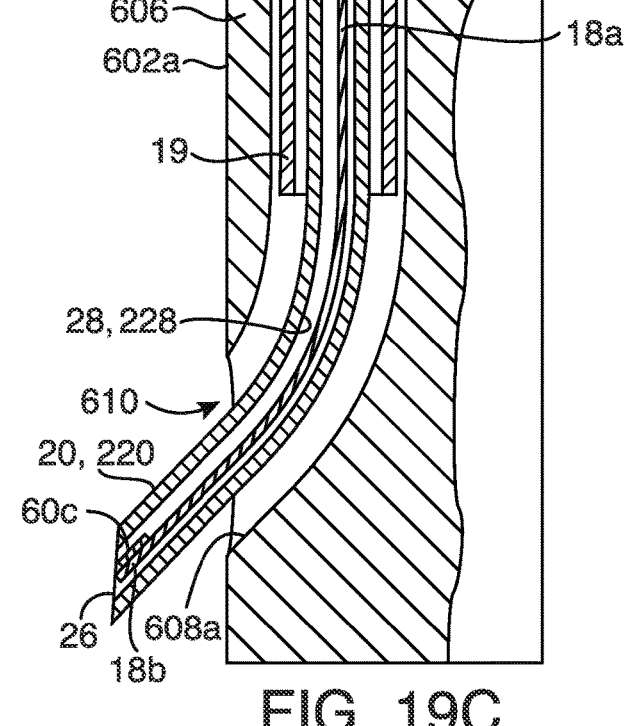
FIG. 19A is a section view of a distal end portion of the medical instrument assembly and the distal end portion of the elongate flexible shaft of the side exit catheter, wherein a third localization element is on or in a flexible guidewire inserted in a lumen of the needle of the medical instrument assembly, wherein the distal end of the flexible guidewire is proximate the tissue piercing distal end portion of the needle according to the embodiment of the invention shown in FIG. 17C.
FIG. 19B is a section view of a distal end portion of the adjustable length medical instrument assembly and the distal end portion of the elongate flexible shaft of the side exit catheter, wherein a third localization element is on or in a flexible guidewire inserted in a lumen of the needle of the adjustable length medical instrument assembly, wherein the distal end of the flexible guidewire is partially retracted from the tissue piercing distal end portion of the needle according to the embodiment of the invention shown in FIG. 17C.
FIG. 19C is a section view of an end portion of the adjustable length medical instrument assembly and the distal end portion of the elongate flexible shaft of the side exit catheter, wherein a third localization element is on or in a flexible guidewire inserted in a lumen of the needle of the adjustable length medical instrument assembly, wherein the distal end of the flexible guidewire is proximate the tissue piercing distal end portion of the needle according to the embodiment of the invention shown in FIG. 17C.

The use of flexible guidewire 18a shown in FIG. 17C (with or without localization element 60c), may be beneficial in the use of needle 20, 220 where needle 20, 220 is a highly flexible needle or includes cuts to increase flexibility of needle 20, 220 (see 22a in FIGS. 16A, 16B). Flexible guidewire 18a may serve two purposes. First, where needle 20, 220 is bendable or flexible as described above, flexible guidewire 18a may provide stiffness to needle 20, 220 as it is being navigated to the target location (see FIGS. 18A, 19A). Flexible guidewire 18a may then be retracted a distance, for example, about 10 mm to about 20 mm, inside lumen 28, 228 of needle 20, 220 to allow needle 20, 220 to bend around a tight turn in an airway A, for example (see FIG. 18B) or through side exit 610 of side-exiting catheter 2600, 3600 (see FIG. 19B). After needle 20, 220 passes around the turn or through side exit, flexible guidewire 18a may then be re-extended so that tip 18b is proximate tissue piercing distal end 26 of needle 20, 220 (see FIGS. 18C, 19C). Second, as described above, localization element 60c on flexible guidewire 18a allows the tissue piercing distal end 26 of needle 20, 220 to be tracked. Once needle 20, 220 has been navigated proximate the desired target, flexible guidewire 18a may be removed from lumens 146c, 118a of medical instrument assembly 110 or lumens 246c, 228 of medical instrument assembly 210 and a sample of the target tissue may be taken through needle 20, 220 via aspiration and/or suction.

Although medical instrument assembly 10 has been described with the use of needle 20, it will be understood that in alternative embodiments a medical instrument assembly 10 may include other medical instruments alternative to needle 20. Such alternative medical devices, include but are not limited to, stents, ablation probes, biopsy devices, forceps devices, brushes, augers, stylets, pointer probes, radioactive seeds, implants, energy delivery devices, therapy delivery devices, devices to deliver energy activated substances (e.g., porfimer sodium) and energy associated devices, radiofrequency (RF) energy devices, cryotherapy devices, laser devices, microwave devices, diffuse infrared laser devices, steam ablation devices, etc. Furthermore, alternative medical instruments may also include a fiber optic cable, a radial endobronchial ultrasound (EBUS) device, optical coherence tomography (OCT) device, or other known imaging devices for visualization and/or diagnosis of the target tissue. Yet another alternative medical instrument may include a microscopy device for visualization and/or diagnosis of the target tissue by evaluating the target tissue at the cellular level. Therefore, it will be understood that imaging devices 208, 2208, 3208 may be used to visualize a variety of these such medical instruments without departing from the scope of the invention.

Additionally, various embodiments that utilize needle 220 with lumen 228, various medical instruments may be inserted into lumen 228 including but not limited to, stents, ablation probes, biopsy devices, forceps devices, brushes, augers, stylets, pointer probes, radioactive seeds, implants, energy delivery devices, therapy delivery devices, devices to deliver energy activated substances (e.g., porfimer sodium) and energy associated devices, radiofrequency (RF) energy devices, cryotherapy devices, laser devices, microwave devices, diffuse infrared laser devices, steam ablation devices, etc. Furthermore, a fiber optic cable, a radial endobronchial ultrasound (EBUS) device, optical coherence tomography (OCT) device, or other known imaging devices may be inserted into lumen 228 of needle 220 for visualization and/or diagnosis of the target tissue. Additionally, a microscopy device may be inserted into lumen 228 of needle 220 for visualization and/or diagnosis of the target tissue by evaluating the target tissue at the cellular level.

Figure 20:
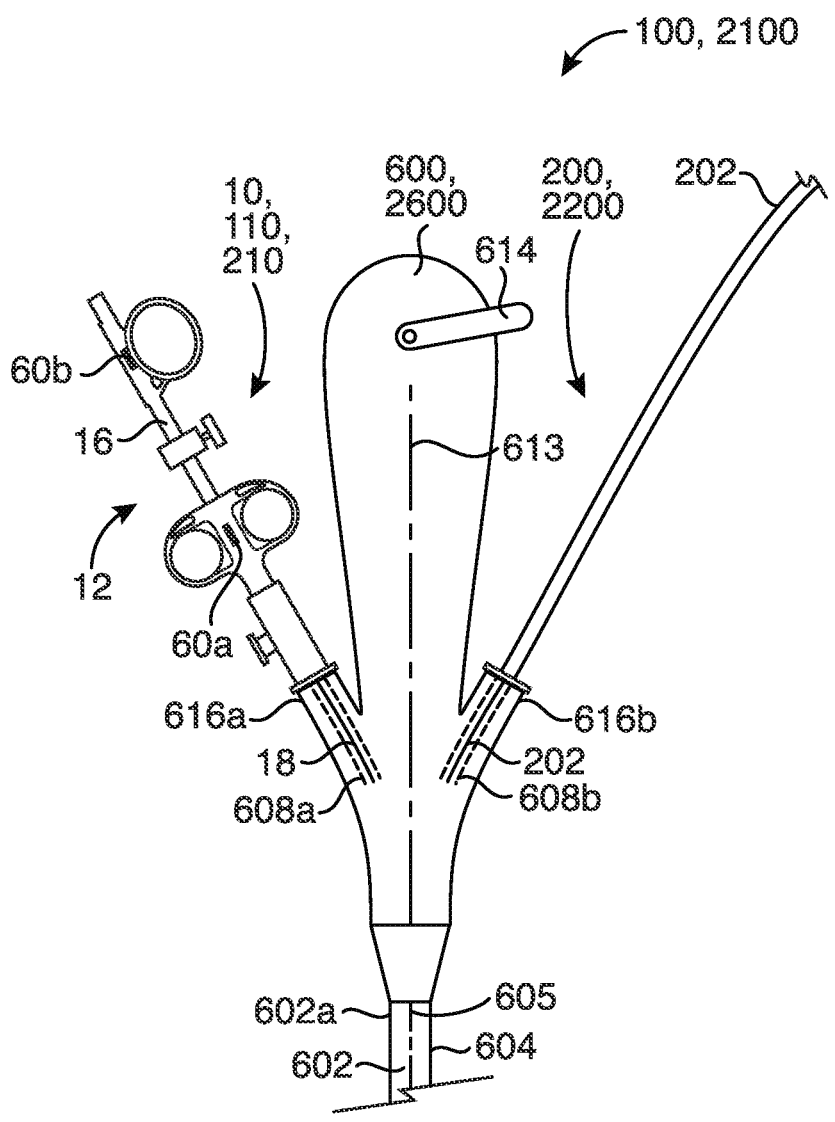
FIG. 20 is a top view of a medical apparatus according to an embodiment of the invention.

While imaging assemblies 200 and 2200 have been described as including handle assemblies 216, it will be understood that in various embodiments, imaging assemblies 200 and 2200 may not require or include handle assemblies 216. That is, in various embodiments, for example, elongate flexible shaft 202 having imaging devices 208 and 2208, may be inserted into working channel 608b of steerable catheter 600 without the use of handle assembly 216 as shown in FIG. 20. The physician or other healthcare professional may simply insert imaging assembly 200, 2200 without handle assembly 216 into second working channel 608b and may extend imaging devices 208, 2208 out second exit 609b to real-time confirm the interception of the target tissue as described in greater detail elsewhere herein without departing from the scope of the invention.

Thus, there has been shown and described novel methods, apparatuses, and systems for generating images of a medical instrument intercepting a target using an imaging device inserted in the patient. It will be apparent, however, to those familiar in the art, that many changes, variations, modifications, and other uses and applications for the subject devices and methods are possible. All such changes, variations, modifications, and other uses and applications that do not depart from the spirit and scope of the invention are deemed to be covered by the invention which is limited only by the claims which follow.

What is claimed:

1. A medical assembly, the medical assembly comprising:
a catheter comprising an elongate flexible shaft having a proximal end portion and a distal end portion, the proximal end portion comprising a port that is fixed in relation to a first catheter handle, the distal end portion comprising a side exit located at an outer wall of the catheter proximate from a distal face of the catheter, wherein a working channel extends between the port and the side exit, and wherein the side exit comprises a side exit ramp having a fixed sloped surface that curves the working channel towards the side exit at an exit angle relative to a longitudinal axis of the catheter;
a medical instrument comprising a proximal end and a distal end and housed within the working channel, the proximal end of the medical instrument comprising a medical instrument handle, the distal end of the medical instrument comprising a needle, the needle having a needle tip that is extendable through the side exit at the exit angle to an extended position beyond the side exit, wherein the side exit ramp causes the needle tip to curve at the exit angle relative to the longitudinal axis of the catheter as it exits through the outer wall; and
an imaging device positioned near the distal end portion of the elongate flexible shaft, wherein the imaging device comprises a radial ultrasound transducer configured to image the needle in the extended position, wherein when the needle is positioned entirely within the working channel the needle tip has an unextended position.

2. The medical assembly of claim 1, further comprising a processor in communication with a display that displays images generated by the imaging device.

3. The medical assembly of claim 1, wherein the side exit is located proximate to a distal most end of the catheter.

4. The medical assembly of claim 1, wherein the distal end portion of the elongate flexible shaft is rotatable within the working channel for orienting the needle such that extension of the needle through the side exit directs the needle toward a target tissue proximate to an airway of a patient.

5. The medical assembly of claim 1, wherein the needle is adapted to intercept a target tissue proximate to an airway of a patient.

6. The medical assembly of claim 1, wherein the imaging device is adapted to generate an image comprising a target tissue proximate to an airway of a patient.

7. The medical assembly of claim 6, wherein the distal end portion of the elongate flexible shaft is adapted to be extended along an airway branch proximate to the target tissue, and wherein the image of the target tissue is generated from within the airway branch.

8. The medical assembly of claim 7, wherein the image depicts the needle intercepting the target tissue when the needle tip is extended beyond the side exit.

9. A medical assembly comprising:

a catheter comprising:

an elongate flexible shaft having a proximal end portion and a distal end portion, a first working channel extending from the proximal end portion to a side exit defining an exit angle relative to a longitudinal axis of the catheter, wherein the side exit is located at an outer wall of the catheter proximate from a distal face of the catheter and comprises a side exit ramp having a fixed sloped surface that curves the working channel towards the side exit at the exit angle, and a second working channel extending from the proximal end portion to the distal end portion;

a medical instrument assembly disposed within the first working channel, the medical instrument assembly comprising:

a handle assembly disposed at a proximal end of the medical instrument assembly, and a needle disposed at a distal end of the medical instrument assembly, the needle having a needle tip that is extendable through the side exit at the exit angle toward a target, wherein the side exit ramp causes the needle tip to curve at the exit angle relative to the longitudinal axis of the catheter as it exits through the outer wall; and an imaging device disposed within the second working channel, the imaging device comprising a radial ultrasound transducer configured to image the needle when the needle tip is extended through the side exit at the exit angle toward the target.

10. The medical assembly of claim 9, wherein the catheter is a non-steerable catheter.

11. The medical assembly of claim 9, wherein the side exit is located proximate to a distal most end of the catheter.

12. The medical assembly of claim 9, wherein the distal end portion of the elongate flexible shaft is rotatable within the working channel for orienting the needle such that extension of the needle through the side exit directs the needle toward with a target tissue proximate to an airway of a patient.

13. The medical assembly of claim 9, wherein the needle is adapted to intercept a target tissue proximate to an airway of a patient.

14. The medical assembly of claim 13, wherein the image depicts the needle intercepting the target tissue when the needle tip is extended beyond the side exit.

15. The medical assembly of claim 14, wherein the distal end portion of the elongate flexible shaft is adapted to be extended along an airway branch proximate to the target tissue, and wherein the image of the target tissue is generated from within the airway branch.

16. A method of generating an image of a medical instrument using a medical apparatus comprising:

providing the medical apparatus, the medical apparatus comprising:

a catheter comprising an elongate flexible shaft having a proximal end portion and a distal end portion, the proximal end portion comprising a port that is fixed in relation to a first catheter handle, the distal end portion comprising a side exit located at an outer wall of the catheter proximate from a distal face of the catheter, wherein a working channel extends between the port and the side exit, and wherein the side exit comprises a side exit ramp having a fixed sloped surface that curves the working channel towards the side exit at an exit angle relative to a longitudinal axis of the catheter;

a medical instrument comprising a proximal end and a distal end and housed within the working channel, the proximal end of the medical instrument comprising a medical instrument handle, the distal end of the medical instrument comprising a needle, the needle having a needle tip that is extendable through the side exit at an exit angle relative to a longitudinal axis of the catheter to an extended position beyond the side exit, wherein the side exit ramp causes the needle tip to curve at the exit angle relative to the longitudinal axis of the catheter as it exits through the outer wall; and an imaging device positioned near the distal end portion of the elongate flexible shaft, and wherein the imaging device comprises a radial ultrasound transducer configured to image the needle in the extended position;

navigating a medical apparatus through an airway of a patient to a position proximate to a target;

extending the needle tip from within the working channel through the side exit; and generating an image of the needle extended beyond the side exit using the imaging device.

17. The method of claim 16, further comprising:

extending the distal end portion of the elongate flexible shaft along an airway branch proximate to a target tissue proximate to an airway of a patient;

extending the needle tip to intercept the target tissue; and generating an image of the needle intercepting the target tissue using the imaging device.

18. The method of claim 17, further comprising:

rotating the distal end portion of the elongate flexible shaft to orient the needle tip such that extension of the needle tip through the side exit directs the needle tip toward the target tissue.

* * * * *